(12) United States Patent
Cho et al.

(10) Patent No.: US 11,080,850 B2
(45) Date of Patent: Aug. 3, 2021

(54) GLAUCOMA DIAGNOSIS METHOD USING FUNDUS IMAGE AND APPARATUS FOR THE SAME

(71) Applicants: ELECTRONICS AND TELECOMMUNICATIONS RESEARCH INSTITUTE, Daejeon (KR); Konyang University Industry-Academic Cooperation Foundation, Nonsan (KR)

(72) Inventors: Hyeon-Sung Cho, Daejeon (KR); Jae-Hoon Jeong, Seoul (KR); Jong-Yeup Kim, Daejeon (KR); Ji-Sang Park, Daejeon (KR)

(73) Assignees: ELECTRONICS AND TELECOMMUNICATIONS RESEARCH INSTITUTE, Daejeon (KR); Konyang University Industry-Academic Cooperation Foundation, Nonsan (KR)

( * ) Notice: Subject to any disclaimer, the term of this patent is extended or adjusted under 35 U.S.C. 154(b) by 321 days.

(21) Appl. No.: 16/246,409

(22) Filed: Jan. 11, 2019

(65) Prior Publication Data

US 2019/0220973 A1 Jul. 18, 2019

(30) Foreign Application Priority Data

Jan. 16, 2018 (KR) .................. 10-2018-0005519
Nov. 5, 2018 (KR) .................. 10-2018-0134333

(51) Int. Cl.
*G06T 7/00* (2017.01)
*G06T 7/13* (2017.01)
(Continued)

(52) U.S. Cl.
CPC ............ *G06T 7/0012* (2013.01); *A61B 3/102* (2013.01); *A61B 3/145* (2013.01); *G06K 9/6267* (2013.01);
(Continued)

(58) Field of Classification Search
CPC .......... G06T 7/0012; G06T 7/13; G06T 7/70; G06T 7/60; G06T 7/136; G06T 7/66;
(Continued)

(56) References Cited

U.S. PATENT DOCUMENTS 7,725,408 B2  5/2010  Lee et al.
8,474,978 B2  7/2013  Huang et al.
(Continued)

FOREIGN PATENT DOCUMENTS

CN    106204555 A  *  12/2016
CN    106529558 A  *   3/2017
(Continued)

OTHER PUBLICATIONS

Asaoka, et al., "Detecting Preperimetric Glaucoma with Standard Automated Perimetry Using a Deep Learning Classifier," Ophthalmology, 2016, vol. 123 (9), pp. 7.
(Continued)

*Primary Examiner* — Matthew C Bella
*Assistant Examiner* — Kathleen M Broughton

(57) ABSTRACT

Disclosed herein are a glaucoma diagnosis method using a fundus image and an apparatus for the same. The glaucoma diagnosis method includes performing data amplification of generating multiple transformed images for an original fundus image based on a preprocessed image of the original fundus image, allowing multiple individual learning models of different types to be learned based on the multiple transformed images and generating a glaucoma determination model based on respective outputs of the learned
(Continued)

multiple individual learning models, and diagnosing a class of glaucoma for the original fundus image based on the glaucoma determination model.

16 Claims, 23 Drawing Sheets

(51) Int. Cl.
| | | |
|---|---|---|
| *G06T 7/70* | (2017.01) | |
| *G06T 7/60* | (2017.01) | |
| *G06K 9/62* | (2006.01) | |
| *A61B 3/14* | (2006.01) | |
| *G06T 7/136* | (2017.01) | |
| *A61B 3/10* | (2006.01) | |
| *G06T 3/60* | (2006.01) | |
| *A61B 3/12* | (2006.01) | |

(52) U.S. Cl.
CPC .............. *G06T 7/13* (2017.01); *G06T 7/136* (2017.01); *G06T 7/60* (2013.01); *G06T 7/70* (2017.01); *A61B 3/12* (2013.01); *G06K 2209/05* (2013.01); *G06T 3/60* (2013.01); *G06T 2207/20081* (2013.01); *G06T 2207/20084* (2013.01); *G06T 2207/30041* (2013.01)

(58) Field of Classification Search
CPC . G06T 2207/30041; G06T 2207/20081; G06T 3/60; A61B 3/102; A61B 3/145; A61B 3/12; G06K 9/6267; G06K 9/6255; G06K 9/4647; G06K 2209/05
See application file for complete search history.

(56) References Cited

U.S. PATENT DOCUMENTS

| | | | |
|---|---|---|---|
| 8,705,826 B2 | 4/2014 | Liu et al. | |
| 9,107,617 B2 | 8/2015 | Liu et al. | |
| 9,173,564 B2 | 11/2015 | Choo et al. | |
| 9,445,716 B2 | 9/2016 | Liu et al. | |
| 9,545,196 B2 | 1/2017 | Abramoff et al. | |
| 9,980,704 B2 | 5/2018 | Gratacós et al. | |
| 2012/0124037 A1 | 5/2012 | Lee et al. | |
| 2013/0077046 A1* | 3/2013 | Kim | G01B 9/02087 351/206 |
| 2014/0268046 A1* | 9/2014 | Narasimha-Iyer | A61B 3/102 351/206 |

FOREIGN PATENT DOCUMENTS

| | | | | |
|---|---|---|---|---|
| CN | 106920227 A | * | 7/2017 | |
| CN | 107045720 A | * | 8/2017 | ........... A61B 3/0025 |
| JP | 2008073280 | | 4/2008 | |
| JP | 2011520503 A | | 7/2011 | |
| KR | 1020160058812 A | | 5/2016 | |
| KR | 101848321 | | 4/2018 | |
| WO | WO-2016064089 A1 | * | 4/2016 | ............... A61B 6/00 |

OTHER PUBLICATIONS

Bourne, et al., "Number of People Blind or Visually Impaired by Glaucoma Worldwide and in World Regions 1990-2010: A Meta-Analysis," PLoS One, 2016, vol. 11 (10), pp. 16.

Chen, et al., "Automatic Feature Learning for Glaucoma Detection Based on Deep Learning," Medical Image Computing and Computer-Assisted Intervention—MICCAI, Part III, 2015, pp. 669-677.

Tham, et al., "Global Prevalence of Glaucoma and Projections of Glaucoma Burden through 2040: A Systematic Review and Meta-Analysis," Ophthalmology, 2014, vol. 121 (11), pp. 2081-2090.

Varma, et al., "An Assessment of the Health and Economic Burdens of Glaucoma," Am J Ophthalmology, 2011, vol. 152 (4), pp. 515-522.

* cited by examiner

GLAUCOMA DIAGNOSIS METHOD USING FUNDUS IMAGE AND APPARATUS FOR THE SAME

CROSS REFERENCE TO RELATED APPLICATIONS

This application claims the benefit of Korean Patent Application Nos. 10-2018-0005519, filed Jan. 16, 2018 and 10-2018-0134333, filed Nov. 5, 2018, which are hereby incorporated by reference in their entirety into this application.

BACKGROUND OF THE INVENTION

1. Technical Field

The present invention relates generally to glaucoma diagnosis technology, and more particularly, to technology for diagnosing a glaucoma class for a fundus image based on a glaucoma determination model.

2. Description of the Related Art

Glaucoma is one of three ophthalmologic diseases causing blindness, together with cataracts and macular degeneration. According to epidemiological investigation of glaucoma conducted in 2014, about 3.54% (64,300,000) of adults worldwide aged 40 or older were glaucoma patients in 2013, and it is estimated that the number of glaucoma patients will increase to 7.6 million in 2020 (Tham et al., 2014). Also, an investigation indicating that the number of glaucoma patients who become blind due to glaucoma all over the world in 2010 has reached 2.1 million and that the number of patients who experienced loss of vision has reached 4.2 million was published (Bourne et al., 2017). In accordance with the results of research into the analysis of glaucoma from an economic standpoint, it is reported that medical expenses personally paid by glaucoma patients have reached 2.9 billion dollars in the United States alone (Varma et al., 2011).

Glaucoma is a disease by which a retinal ganglion cell (RGC) and an axon thereof are damaged, thus causing a patient to become blind. Since glaucoma has the characteristics of chronic and irreversible progression, the progression of glaucoma that is detected in an early stage can be delayed through medication or surgery, and the effect of treatment thereof is relatively good. However, there are many cases where subjective symptoms that can be clearly felt by patients, such as visual field defects or the deterioration of eyesight, do not appear until the last stage of glaucoma due to the characteristics of the disease. Further, when glaucoma in later stages is serious, the prognosis thereof is bad, and thus the importance of early detection through examination is very high.

Currently, as representative methods for diagnosing glaucoma, there are diagnosis methods such as Scanning laser Polarimetry (SLP), Optical Coherence tomography (OCT), a visual field test, and a comparison of the cup-to-disc ratio of an Optic Disc (OD).

Diagnosis using OCT illustrated in FIG. 1 is a method of measuring the thickness of an optic nerve fiber layer, and is advantageous in that quantification and objectification are possible, but there is a limitation in detecting a lesion related to glaucoma that is present outside a capture area because this method measures only a Retinal Nerve Fiber Layer (RNFL) present in a very limited area from the Optic Disc (OD). Further, in the case of preperimetric glaucoma or early glaucoma, a defect in an RNFL exhibits a phase in which it starts at the optic disc and extends to the peripheral portion of the retina. Therefore, an RNFL defect in an optic disc area, which meaningfully appears in the results of OCT measurement, makes it difficult to diagnose early glaucoma.

The visual field test illustrated in FIG. 2 is a method for measuring whether a patient has a visual field micro-defect, and it is widely used to definitively diagnose glaucoma, but it is disadvantageous in that it takes a lot of time and effort in measurement and in that consistency in measurement of early glaucoma is deteriorated. Also, similar to OCT, ability to diagnose preperimetric glaucoma is limited. At the University of Tokyo in 2016, cases of application of deep learning using data resulting from visual field tests were published (Asaoka et al., 2016). The visual field test is disadvantageous in that it generally requires a test time of 30 minutes or longer and in that both the patient and the medical team that conducts the test must make a lot of effort during the test process. Further, since equipment for the visual field test is more expensive than a fundus scope, medical accessibility is not good from the standpoint of the adoption of the required equipment in the medical field, and it is thus difficult to perform glaucoma screening tests at low cost. Also, there is limited ability to detect preperimetric glaucoma in cases in which a visual field defect does not occur. Research conducted by Asaoka et al. (2016) did not take into consideration the issue of classification of severity of glaucoma.

Chen et al. (2015) presented a method for extracting an Optic Disc (OD) area from a fundus image and applying the OD area to deep learning in order to automatically diagnose glaucoma. However, research conducted by Chen et al. (2015) is disadvantageous in that only the OD area of the fundus image is applied to deep learning. That is, since the situation in which a lesion related to glaucoma can be identified from the OD area of the fundus image appears in the middle stage or subsequent stages of glaucoma in most cases, there is a limitation in the extent to which preperimetric glaucoma or early glaucoma can be detected. Further, issues related to the classification of severity of glaucoma are not addressed.

As illustrated in FIG. 3, a conventional method for diagnosing glaucoma using an OD area of a fundus image is to calculate a Cup-to-Disc Ratio (CDR) in the OD area forming a neuron from the OD forming a bundle of nerves. Such a CDR method is also disadvantageous in that it is difficult to identify preperimetric glaucoma and early glaucoma and in that there is a limitation in quantifying the severity of glaucoma because the method diagnoses glaucoma using a very limited area, such as the OD.

In contrast, an anatomical structure in which a defect occurs first at the early stage of glaucoma is a Retinal Nerve Fiber Layer (RNFL) composed of axons of ganglion cells. In consideration of these pathological characteristics, it is very important to determine whether there is an RNFL defect through a fundus photography test conducted in a health medical examination or an eye examination, and then detect the symptoms of glaucoma early on. In a fundus image captured from the retina of an early glaucoma patient, a local wedge-shaped RNFL defect may be checked for. Typically, the task of accurately identifying an RNFL defect from the fundus image with the naked eye is a very difficult task that may be performed only by a highly-skilled eye specialist.

Consequently, to date, deep-learning research into technology for providing the ability to automatically detect preperimetric glaucoma and early glaucoma using the entire fundus image while providing a function of classifying the severity of glaucoma has not yet been published.

PRIOR ART DOCUMENTS

Patent Documents (Patent Document 1) Korean Patent No. 10-1848321, Date of Publication: Apr. 20, 2018 (title: "Method for Facilitating Diagnosis of Subject Based on Fovea Image thereof and Apparatus Using the Same")

SUMMARY OF THE INVENTION

Accordingly, the present invention has been made keeping in mind the above problems occurring in the prior art, and an object of the present invention is to provide a glaucoma diagnosis method, which enables a screening test for preperimetric glaucoma and early glaucoma based on a fundus image, which has excellent medical accessibility while decreasing diagnostic test costs.

Another object of the present invention is to classify and diagnose the severity of glaucoma by automatically identifying a micro-defect in a Retinal Nerve Fiber Layer (RNFL) based on a deep-learning model that is capable of automatically classifying the severity of glaucoma.

A further object of the present invention is to improve the quality of medical service in the future by providing technology that is capable of classifying the severity of glaucoma and to decrease social costs attributable to blindness by decreasing the risk of blindness while reducing the expenditure of related medical costs.

Still another object of the present invention is to provide a glaucoma diagnosis function in the form of artificial intelligence-based Clinical Decision Support System (CDSS) software, which can be installed in a fundus scope, which is currently and widely popularized, or can be operated in conjunction with the fundus scope, thus enabling the glaucoma diagnosis function to be utilized in various fields.

Yet another object of the present invention is to provide glaucoma diagnosis technology that can be utilized for an automated service for a glaucoma screening test, improve the efficiency and accuracy of reading the results of fundus photography (ophthalmography) conducted on a large scale, and pass the time-saving benefit obtained from such improvement on to a specialist performing secondary determination, thus resulting in a more economical and accurate medical examination.

In accordance with an aspect of the present invention to accomplish the above objects, there is provided a glaucoma diagnosis method, including performing data amplification of generating multiple transformed images for an original fundus image based on a preprocessed image of the original fundus image; allowing multiple individual learning models of different types to be learned based on the multiple transformed images and generating a glaucoma determination model based on respective outputs of the learned multiple individual learning models; and diagnosing a class of glaucoma for the original fundus image based on the glaucoma determination model.

Performing the data amplification may include designating multiple capture areas for generating the multiple transformed images within a range preset based on an optic disc detected from the preprocessed image.

Each of the multiple capture areas may have a shape of a square, having sides of a preset length, in consideration of a size of the optic disc and have a center of gravity thereof located on a circumference of a virtual circle having a center of the optic disc as a center of the virtual circle, wherein a radius of the virtual circle is greater than that of a circle corresponding to a boundary of the optic disc.

Output grades of the multiple individual learning models may be equal to or greater than a third grade having at least three outputs.

Generating the glaucoma determination model may be configured to generate the glaucoma determination model based on a matrix into which respective outputs of the learned multiple individual learning models are digitized and integrated.

Designating the multiple capture areas may be configured to set any one point on the circumference of the virtual circle as a reference point and to set multiple centers of gravity corresponding to the multiple capture areas while moving at a preset angle from the reference point.

Performing the data amplification may be configured to generate multiple captured images by capturing images of the multiple capture areas and generate the multiple transformed images by performing rotation and channel separation on each of the multiple captured images.

Performing data amplification may further include binarizing the preprocessed image into a binary image and estimating the center and the boundary of the optic disc based on respective summation vectors of a horizontal axis and a vertical axis of a matrix indicating pixel values of the binary image.

Estimating the center and the boundary of the optic disc may be configured to estimate coordinates of the center in accordance with a maximum value of the summation vector of the horizontal axis and a maximum value of the summation vector of the vertical axis and to estimate a radius of the circle corresponding to the boundary based on a remaining portion, other than portions in which values in respective summation vectors of the horizontal axis and the vertical axis correspond to '0'.

The multiple individual learning models may correspond to Convolutional Neural Networks (CNN) and may be different from each other in at least one of a number of hidden layers in a corresponding CNN, a type of input data, and a number of outputs.

The glaucoma diagnosis method may further include performing preprocessing of generating the preprocessed image by respectively detecting a fundus-left tangent line and a fundus-right tangent line based on two-dimensional (2D) matrix values generated based on binarized pixel values of the original fundus image and by deleting an unnecessary area that does not include information about the fundus with respect to the left tangent line and the right tangent line.

In accordance with another aspect of the present invention to accomplish the above objects, there is provided a glaucoma diagnosis apparatus, including a preprocessing unit for generating a preprocessed image of an original fundus image; a data amplification unit for generating multiple transformed images for the original fundus image based on the preprocessed image; a glaucoma determination model generation unit for allowing multiple individual learning models of different types to be learned based on the multiple transformed images and generating a glaucoma determination model based on respective outputs of the learned multiple individual learning models; a processing unit for diagnosing a class of glaucoma for the original fundus image based on the glaucoma determination model; and a storage unit for storing the multiple individual learning models and the glaucoma determination model.

The data amplification unit may designate multiple capture areas for generating the multiple transformed images within a range preset based on an optic disc detected from the preprocessed image.

Each of the multiple capture areas may have a shape of a square, having sides of a preset length, in consideration of a size of the optic disc and have a center of gravity thereof located on a circumference of a virtual circle having a center of the optic disc as a center of the virtual circle, wherein a radius of the virtual circle is greater than that of a circle corresponding to a boundary of the optic disc.

Output grades of the multiple individual learning models may be equal to or greater than a third grade having at least three outputs.

The glaucoma determination model generation unit may generate the glaucoma determination model based on a matrix into which respective outputs of the learned multiple individual learning models are digitized and integrated.

The data amplification unit may set any one point on the circumference of the virtual circle as a reference point, and set multiple centers of gravity corresponding to the multiple capture areas while moving at a preset angle from the reference point.

The data amplification unit may generate multiple captured images by capturing images of the multiple capture areas, and generate the multiple transformed images by performing rotation and channel separation on each of the multiple captured images.

The data amplification unit may binarize the preprocessed image into a binary image and estimate the center and the boundary of the optic disc based on respective summation vectors of a horizontal axis and a vertical axis of a matrix indicating pixel values of the binary image.

The data amplification unit may estimate coordinates of the center in accordance with a maximum value of the summation vector of the horizontal axis and a maximum value of the summation vector of the vertical axis, and estimate a radius of the circle corresponding to the boundary based on a remaining portion, other than portions in which values in respective summation vectors of the horizontal axis and the vertical axis correspond to '0'.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
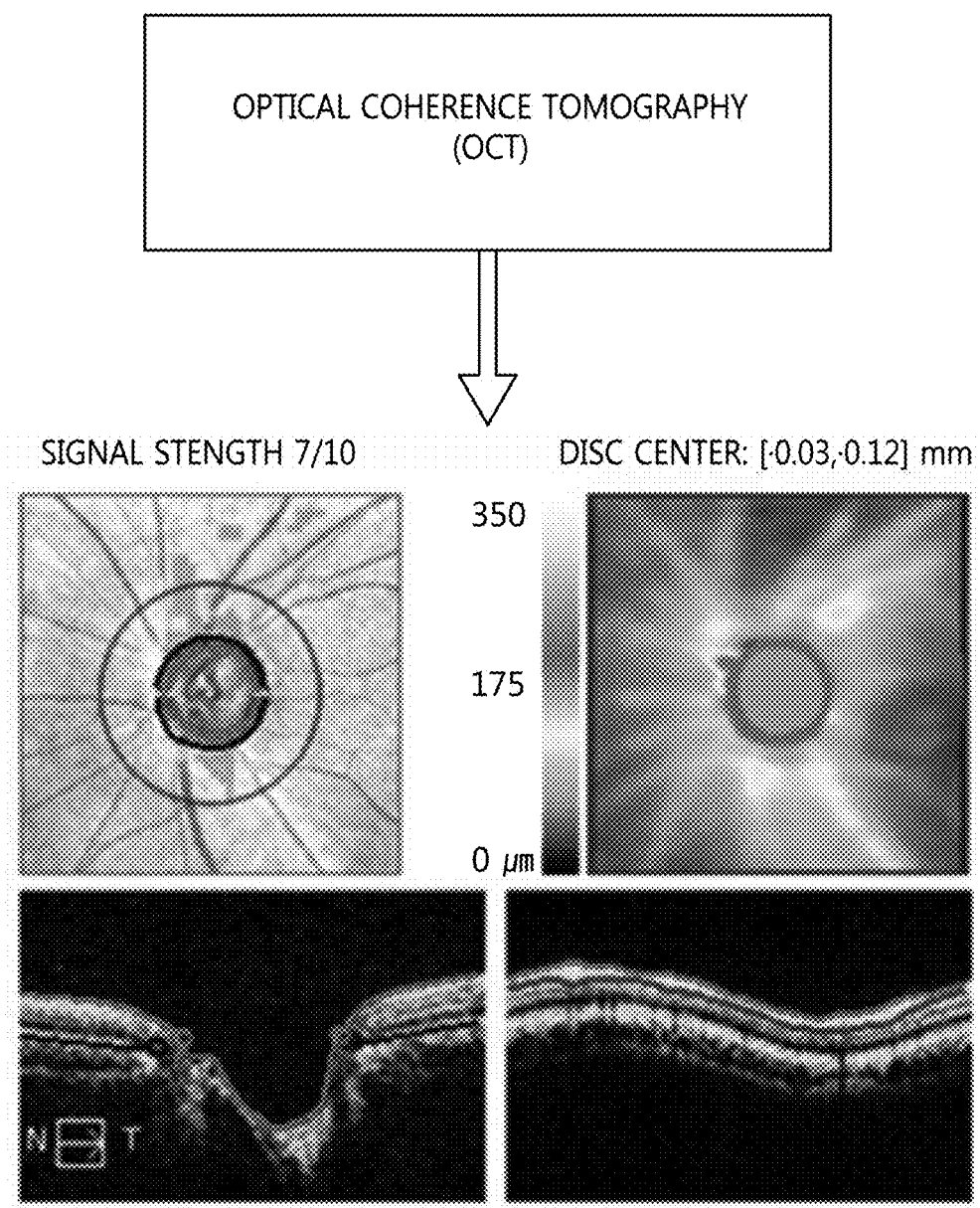
FIGS. 1 to 3 are diagrams illustrating examples of a conventional glaucoma diagnosis method.
Figure 2:
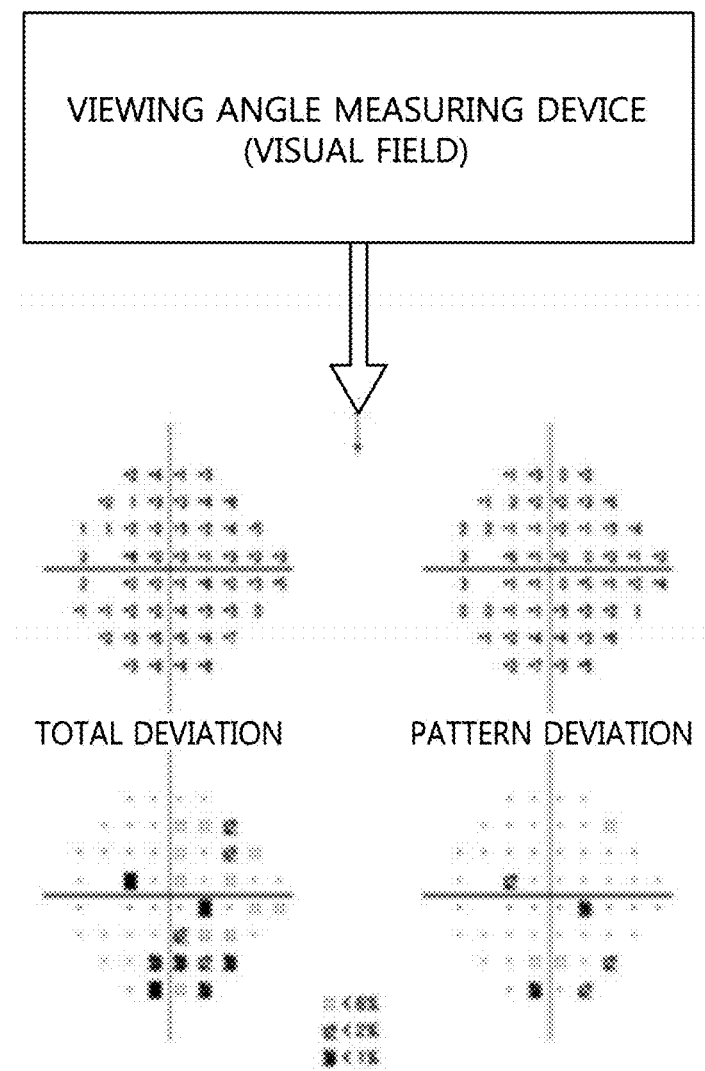
Figure 3:
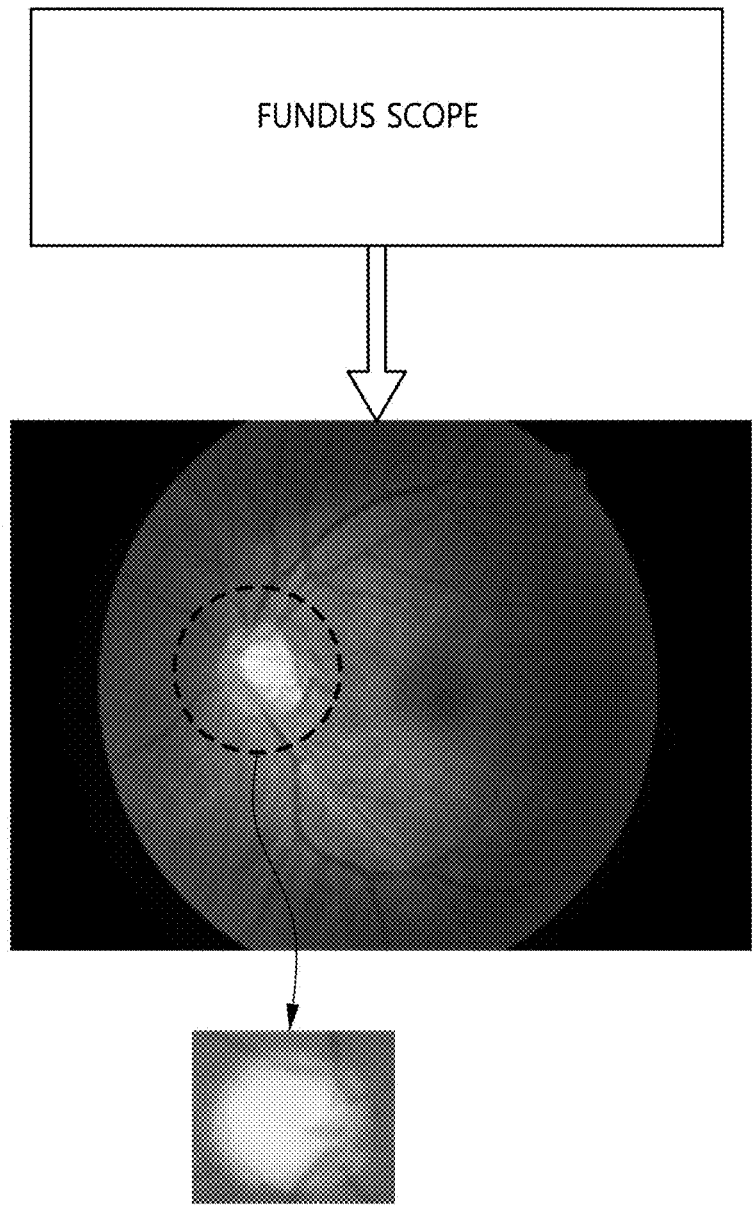

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, preferred embodiments of the present invention will be described in detail with reference to the attached drawings.

Figure 4:
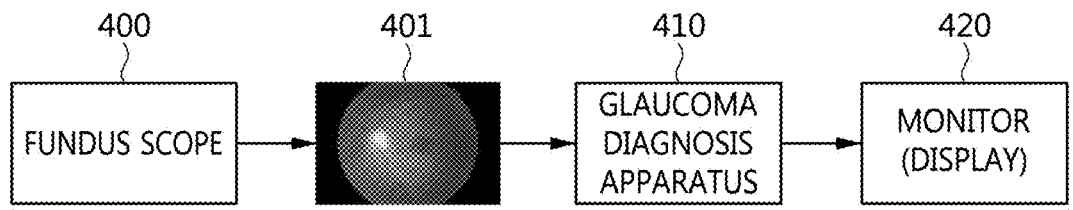
FIG. 4 is a diagram illustrating a glaucoma diagnosis system according to an embodiment of the present invention.

FIG. 4 is a diagram illustrating a glaucoma diagnosis system according to an embodiment of the present invention.

Referring to FIG. 4, the glaucoma diagnosis system according to the embodiment of the present invention includes a fundus scope 400, a glaucoma diagnosis apparatus 410, and a monitor 420.

Fundus photography equipment, which is currently universally used, does not provide a function of automatically identifying a micro-defect in a Retinal Nerve Fiber Layer (RNFL), which enables early detection of glaucoma. When this situation and the characteristics of a disease called "glaucoma" are taken into consideration, there is urgently required the development of technology that is capable of performing an automated screening test for glaucoma diagnosis, classifying the severity of glaucoma, and also detecting preperimetric glaucoma and early glaucoma.

Therefore, the present invention is intended to provide the glaucoma diagnosis apparatus 410 that is capable of automatically determining whether there is an RNFL defect occurring from a preperimetric glaucoma stage and from an early glaucoma stage and is capable of classifying the severity of glaucoma.

The glaucoma diagnosis apparatus 410 according to the embodiment of the present invention generates multiple transformed images for an original fundus image 401 based on a preprocessed image of the original fundus image 401.

Here, the original fundus image 401 may be acquired by capturing an image of the eye of a glaucoma diagnosis patient using a fundus scope 400.

The glaucoma diagnosis apparatus 410 may generate the preprocessed image by individually detecting a left tangent line and a right tangent line of a fundus based on 2D matrix values generated based on binarized pixel values of the original fundus image 401 and by deleting an unnecessary area that does not contain fundus information with respect to the left tangent line and the right tangent line.

Here, multiple capture areas for generating multiple transformed images may be designated within a preset range based on an optic disc detected from the preprocessed image.

Each of the multiple capture areas may have the shape of a square having sides of a preset length in consideration of the size of the optic disc and has the center of gravity thereof located on the circumference of a virtual circle having the center of the optic disc as the center of the virtual circle, wherein the radius of the virtual circle may be greater than that of a circle corresponding to the boundary of the optic disc.

Here, the preprocessed image may be binarized into a binary image, and the center and the boundary of the optic disc may be estimated based on respective summation vectors of the horizontal axis and the vertical axis of a matrix that indicates the pixel values of the binary image.

The coordinates of the center may be estimated in accordance with the maximum value of the summation vector of the horizontal axis and the maximum value of the summation vector of the vertical axis, and the radius of the circle corresponding to the boundary may be estimated based on the remaining portions of the summation vectors, other than portions in which the values of the summation vectors of the horizontal axis and the vertical axis correspond to '0'.

Here, any one point on the circumference of the virtual circle may be set as a reference point, and multiple centers of gravity corresponding to the multiple capture areas may be set while moving at a preset angle from the reference point.

Multiple captured images may be generated by capturing images of the multiple capture areas, and multiple transformed images may be generated by performing rotation and channel separation on each of the multiple captured images.

Also, the glaucoma diagnosis apparatus 410 according to the embodiment of the present invention allows different types of multiple individual learning models to be learned based on the multiple transformed images, and generates a glaucoma determination model based on respective outputs of the learned multiple individual learning models.

Here, the output grades of the multiple individual learning models may be a third grade or more having at least three outputs.

At this time, the multiple individual learning models may be Convolutional Neural Networks (CNN), and may be different from each other in at least one of the number of hidden layers in the corresponding CNN, the type of input data, and the number of outputs.

Next, the glaucoma diagnosis apparatus 410 according to the embodiment of the present invention diagnoses a glaucoma class for the original fundus image 401 based on the glaucoma determination model.

In this case, the glaucoma determination model may be generated based on a matrix obtained by digitizing and integrating respective outputs of the learned multiple individual learning models.

Here, when the diagnosis of glaucoma is completed using the glaucoma determination model, the glaucoma class may be output to a doctor or the glaucoma diagnosis patient via the monitor 420.

The glaucoma diagnosis apparatus 410 may decrease the ratio of risk of blindness by improving the quality of medical service and reducing the expenditure of related medical costs, and thus an effect of reducing social costs attributable to blindness may be expected.

Next, when the glaucoma diagnosis apparatus 410 according to the embodiment of the present invention is utilized for a medical examination and an eye examination, a great ripple effect on medical device markets may be expected. For example, the results of research provided according to the present invention correspond to artificial intelligence-based Clinical Decision Support System (CDSS) software, and this type of CDSS may be utilized in the state of being installed in the fundus scope 400, which is currently and widely popularized, or to be operated in conjunction with the fundus scope 400.

Further, a fundus photography test, which is basically included in most medical examination checklists, may be performed in conjunction with the glaucoma diagnosis apparatus 410 according to the embodiment of the present invention, and thus it may be utilized for an automated service for a glaucoma screening test. Through this utilization, the efficiency and accuracy of reading the results of fundus photography (ophthalmography) conducted on a large scale may be improved, and the time-saving benefit obtained from such improvement may be passed on to a specialist performing secondary determination, thus resulting in a more economical and accurate medical examination to the diagnosis patient.

Furthermore, when the glaucoma diagnosis apparatus 410 according to the embodiment of the present invention is utilized in an eye care field, variation in the state of the retina of a patient over time may be objectively monitored (based on a comparison), thus effectively responding to a glaucoma disease, which is a chronic and irreversible disease.

Furthermore, since glaucoma can be detected in an early stage, medical decision-making for definitely diagnosing or closely monitoring glaucoma may be prevented from being delayed, thus reducing medical costs to be paid by patients. In addition, glaucoma may be detected and treated early on, and thus an improvement in treatment effect may also be expected.

Furthermore, when glaucoma is detected in an early stage, the ratio of risk of blindness of patients may be decreased by up to 95%, and thus the effect of decreasing additional social loss costs may be expected.

Figure 5:
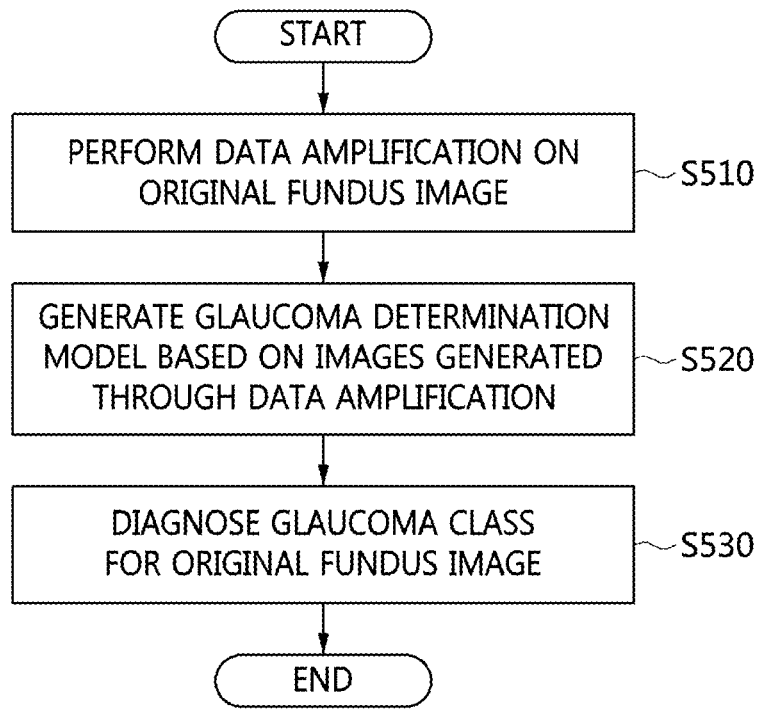
FIG. 5 is an operation flowchart illustrating a glaucoma diagnosis method according to an embodiment of the present invention.

FIG. 5 is an operation flowchart illustrating a glaucoma diagnosis method according to an embodiment of the present invention.

Referring to FIG. 5, in the glaucoma diagnosis method according to the embodiment of the present invention, multiple transformed images for an original fundus image are generated based on a preprocessed image of the original fundus image at step S510.

Figure 6:
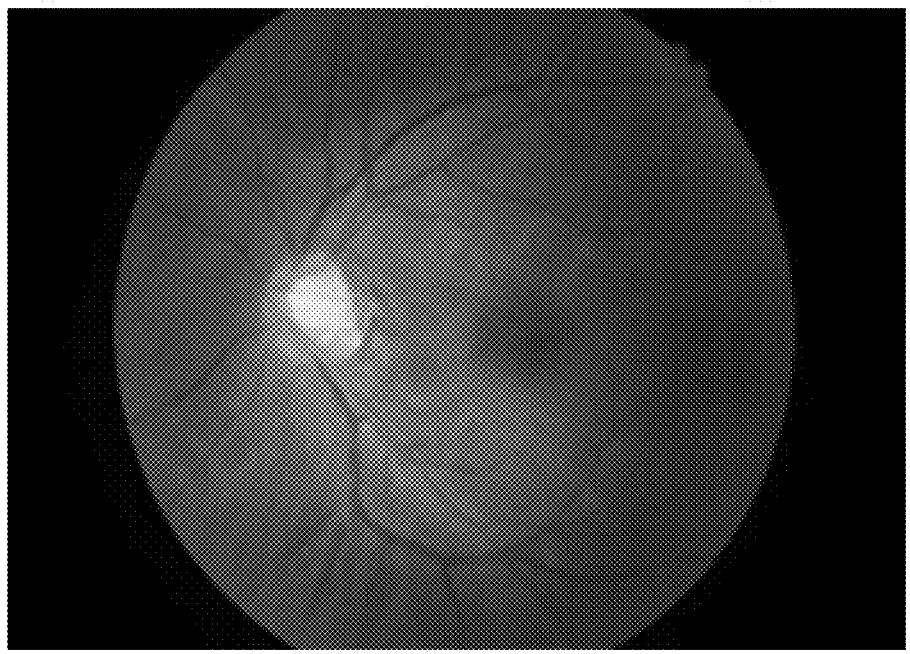
FIG. 6 is a diagram illustrating an example of an original fundus image according to an embodiment of the present invention.

Here, the original fundus image may be an image obtained by capturing an image of the retina of a patient using a fundus scope or a fundus camera, and may be captured as illustrated in FIG. 6.

In this case, the original fundus image, such as that illustrated in FIG. 6, may be a three-channel color image, and may be data that is basically input in order to determine whether glaucoma is present or to classify the severity of glaucoma.

Here, the preprocessed image may be generated through a procedure of performing preprocessing on the original fundus image. Such a preprocessing procedure may be configured to eliminate unnecessary information present in the original fundus image and to convert the original fundus image into information in a state usable for machine learning for diagnosing glaucoma.

Although not illustrated in FIG. 5, the glaucoma diagnosis method according to the embodiment of the present invention may generate the preprocessed image by individually detecting a left tangent line and a right tangent line of a fundus based on 2D matrix values generated based on binarized pixel values of the original fundus image and by deleting unnecessary areas that do not contain fundus information with respect to the left tangent line and the right tangent line.

Figure 7:
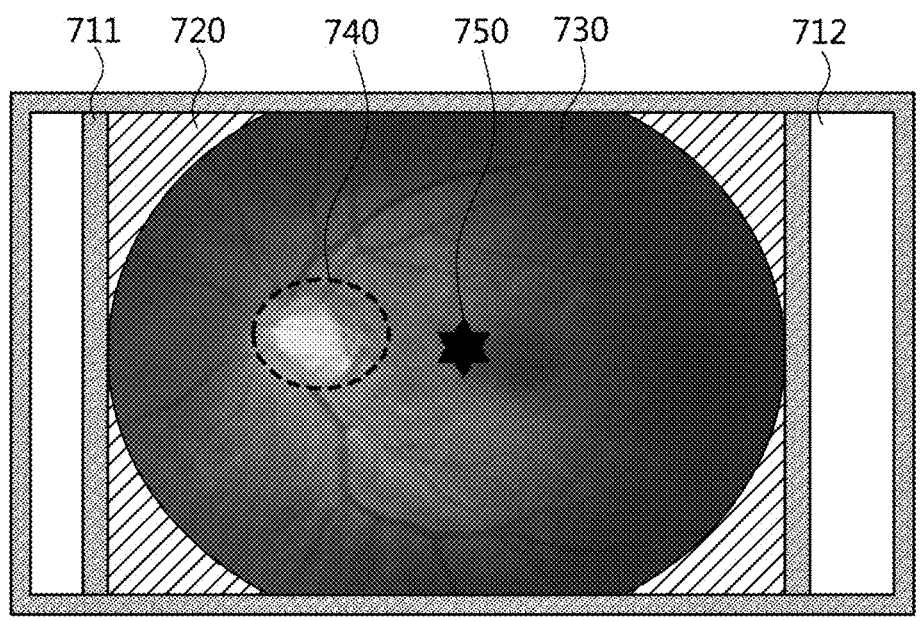
FIG. 7 is a diagram illustrating an example of information recognized in a preprocessing procedure according to the present invention.

For example, the preprocessing procedure may be a procedure for recognizing information about a fundus-left tangent line 711, a fundus-right tangent line 712, an information non-inclusion area 720, a fundus area 730, an optic disc 740, and a fundus center 750, which are included in the original fundus image, as illustrated in FIG. 7, and for deleting areas unnecessary for the determination of glaucoma based on the recognized information.

Here, the unnecessary areas may mean areas located outside the fundus-left tangent line 711 and the fundus-right tangent line 712 illustrated in FIG. 7, that is, areas that do not contain fundus information. Therefore, as illustrated in FIG. 8, the preprocessed image may be generated by deleting unnecessary areas 811 and 812 that do not contain fundus information.

Figure 8:
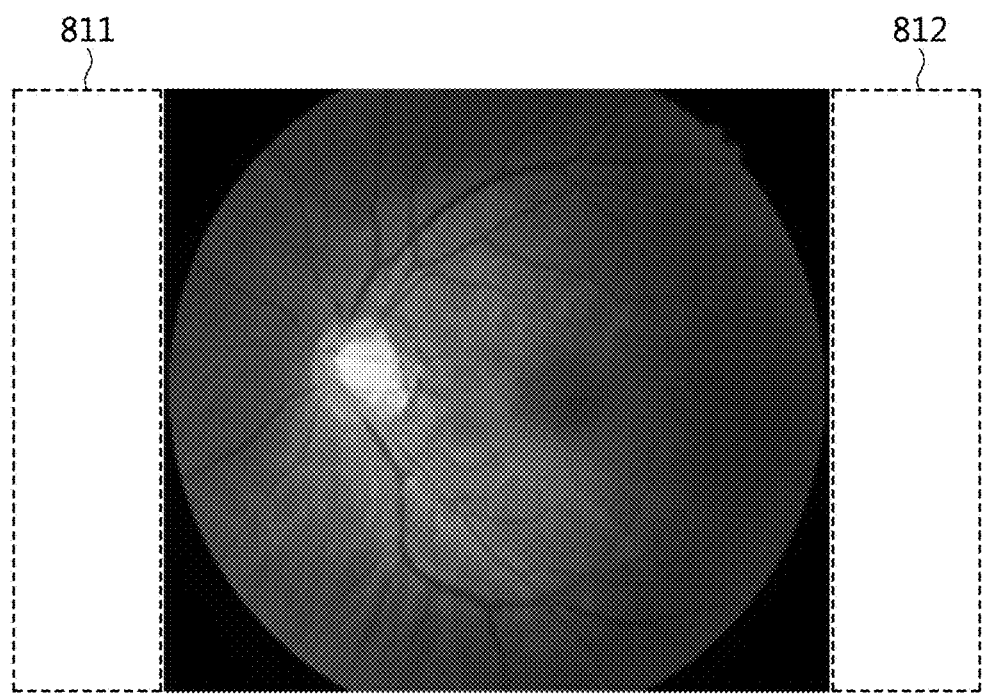
FIG. 8 is a diagram illustrating an example of a preprocessed image according to the present invention.

Although the information non-inclusion area 720 illustrated in FIG. 7 does not contain fundus information, similar to the unnecessary areas 811 and 812 illustrated in FIG. 8, it is located inside the fundus-left tangent line 711 and the fundus-right tangent line 712, and thus the information non-inclusion area 720 is not deleted in the preprocessing procedure. Therefore, the information non-inclusion area 720 may be utilized for indicating separate marking information such as the image number or capture date of the corresponding fundus image.

The core of the preprocessing procedure is to detect the fundus-left tangent line and the fundus-right tangent line from the original fundus image and to extract an area therebetween.

Therefore, with reference to FIGS. 9 to 11, a procedure for detecting the fundus-left tangent line and the fundus-right tangent line from the original fundus image will be described in detail below.

Figure 9:
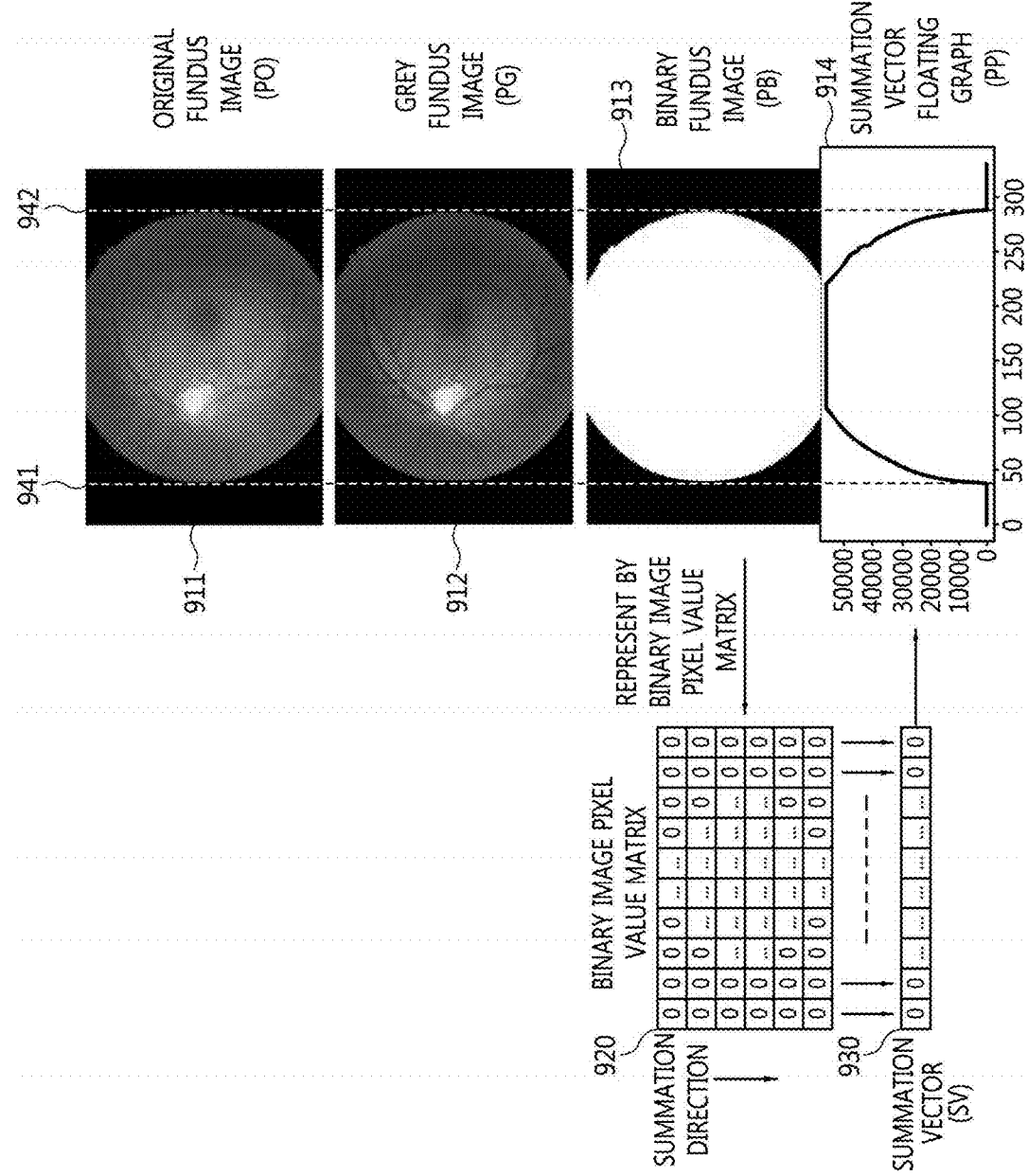
FIGS. 9 to 11 are diagrams illustrating examples of a procedure for extracting a fundus boundary in a preprocessing procedure according to the present invention.
Figure 10:
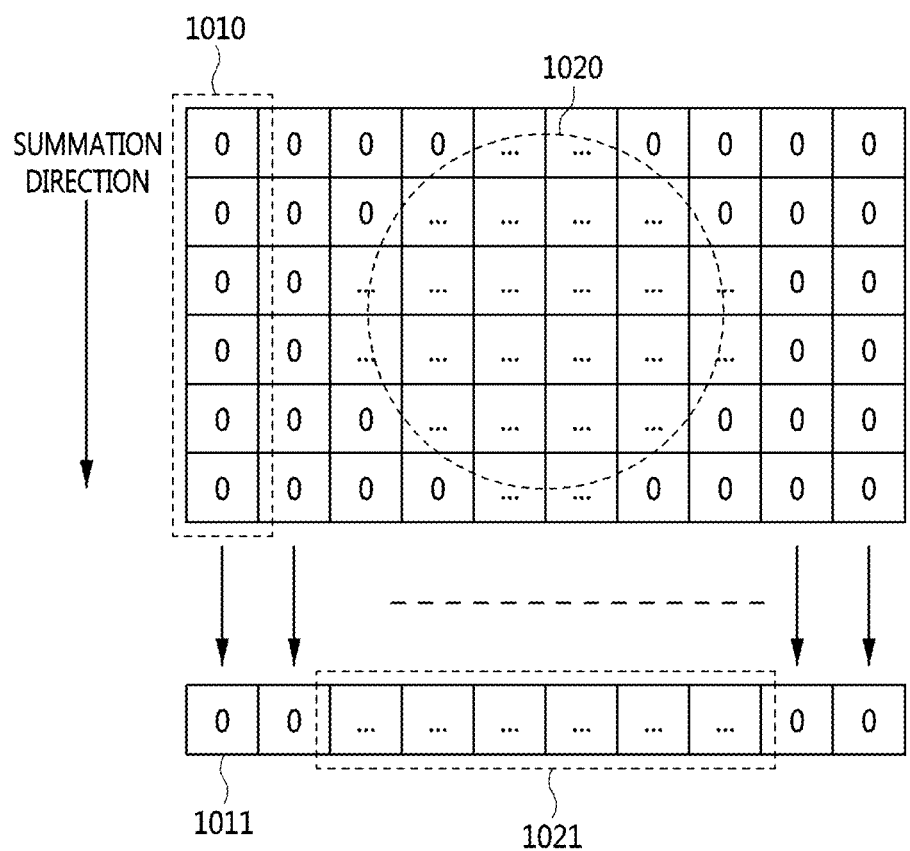

First, referring to FIG. 9, an original fundus image (Picture Original: PO) 911 may be converted into the format of a grey fundus image (Picture Grey: PG) 912. Here, data of the grey fundus image 912 may have a 2D matrix structure. Therefore, the matrix may be binarized back based on a specific threshold value (ThresHoldBinary: THB), and may be converted into a binary fundus image (Picture Binary: PB) 913. Since the binary fundus image 913 may also have a 2D matrix data structure, the pixels of the binary fundus image 913 may be represented by a matrix, that is, a binary image pixel value matrix 920. In this case, as illustrated in FIG. 10, values in the binary image pixel value matrix are summed in the direction of a horizontal axis, and a horizontal axis summation vector 930 corresponding to the results of summation in the horizontal axis may float on a 2D plane, and thus a horizontal axis summation vector floating graph 914 may be acquired. Here, referring to the summation vector 930 or the horizontal axis summation vector floating graph 914, it can be seen that all values except for values in the fundus area 730, such as that shown in FIG. 7, appear as '0'. That is, a portion in which a summation column vector value 1011, obtained by summing values in a summation column 1010, as shown in FIG. 10, is '0' means that fundus information is not included in the portion corresponding to the summation column 1010 in the original fundus image 911, and may then be determined to be an unnecessary area.

Figure 11:
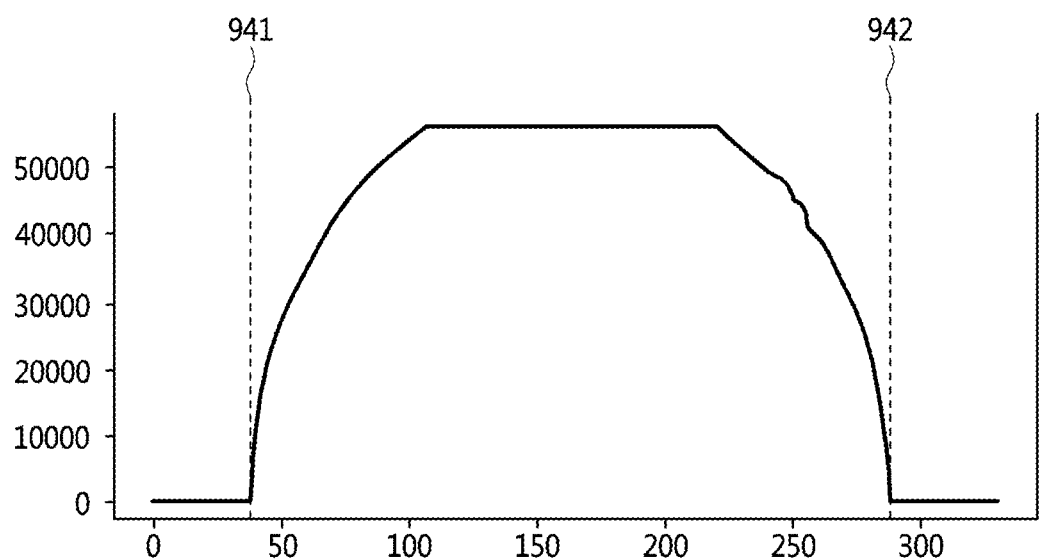

Therefore, as illustrated in FIG. 11, portions in which the value of the horizontal axis summation vector changes to be greater than 0 in the horizontal axis summation vector floating graph 914 may be detected as the locations of a fundus-left tangent line 941 and a fundus-right tangent line 942. Here, a portion detected first on the left side of a floating line in the horizontal axis summation vector floating graph 914 is determined to be the location of the fundus-left tangent line 941, and a portion detected first on the right side of the floating line is determined to be the location of the fundus-right tangent line 942.

Also, in the present invention, a data amplification task for receiving the preprocessed image, acquired through the above-described preprocessing procedure, as input and generating multiple transformed images may be performed.

Here, the purpose of data amplification is to provide learning data required in order to allow model parameters, which are targets to be optimized, to be sufficiently learned during a process for constructing the glaucoma determination model. Also, the effect of eliminating dependence of the glaucoma determination model on specific data may be expected by providing various types of learning data based on data amplification.

The task to be performed first for data amplification is to detect an optic disc from the preprocessed image and estimate an external boundary line of the optic disc. That is, in the present invention, whether an RNFL defect is present must be determined in order to detect preperimetric glaucoma or early glaucoma. In this case, the RNFL may correspond to the optic nerve, and the optic disc may correspond to a portion in which the retina is connected to the optic nerve, and thus the approximate location of the RNFL may be determined by detecting the optic disc from the preprocessed image.

Figure 12:
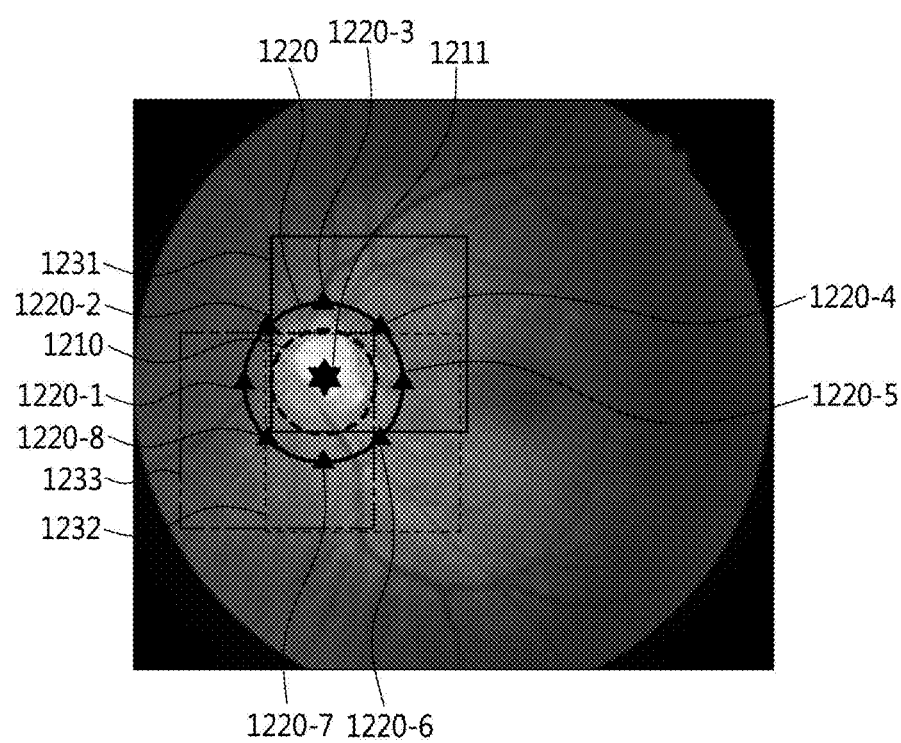
FIGS. 12 to 14 are diagrams illustrating examples of a procedure for extracting the center and the boundary of an optic disc according to the present invention.

Here, the optic disc may correspond to the brightest portion, among portions of the fundus image included in the preprocessed image, as illustrated in FIG. 12. Below, a procedure for estimating the center and the boundary of the optic disc from the preprocessed image will be described in detail with reference to FIGS. 13 and 14.

First, the preprocessed image may be binarized into a binary image, and the center and boundary of the optic disc may be estimated based on respective summation vectors of the horizontal axis and the vertical axis of a matrix that indicates the pixel values of the binary image.

Figure 13:
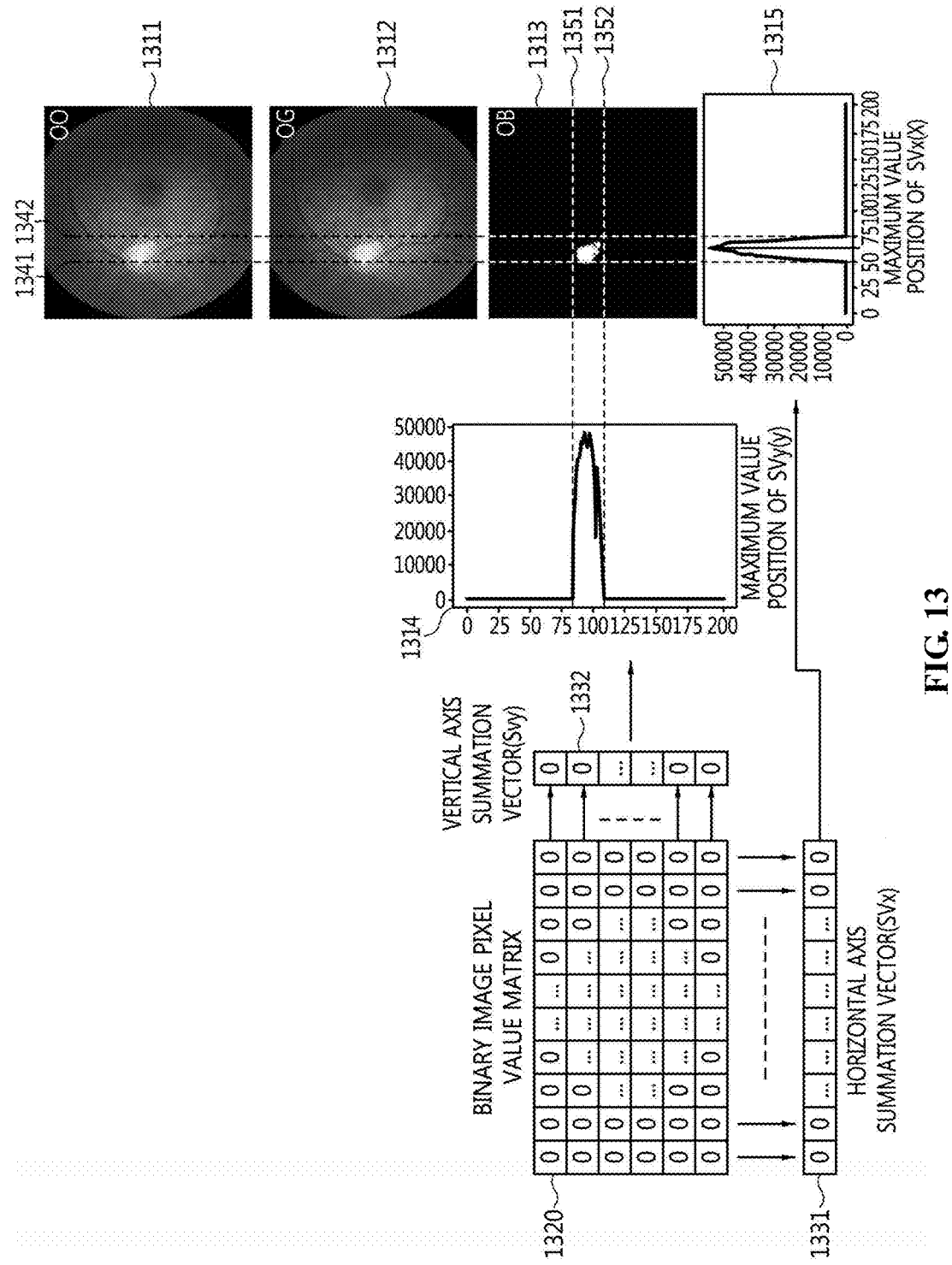

For example, referring to FIG. 13, a preprocessed image 1311 may be converted into a grey preprocessed image (picture grey) 1312. Here, the data of the grey preprocessed image 1312 may have a 2D matrix structure. Therefore, the matrix is binarized back based on a specific threshold value THO, and may then be converted into a binary preprocessed image 1313. Here, since the binary preprocessed image 1313 may also have a 2D matrix data structure, the pixels of the binary preprocessed image 1313 are represented by a matrix, that is, a binary image pixel value matrix 1320.

Here, as illustrated in FIG. 13, values in the binary image pixel value matrix 1320 may be respectively summed for a horizontal axis and a vertical axis, and a horizontal axis summation vector 1331 and a vertical axis summation vector 1332, which correspond to respective summed results, may float on a 2D plane, and thus a horizontal axis summation vector floating graph 1315 and a vertical axis summation vector floating graph 1314 may be acquired.

Thereafter, the coordinates of the center of the optic disc may be estimated in accordance with the maximum value of the horizontal axis summation vector and the maximum value of the vertical axis summation vector. The radius of a circle corresponding to the boundary of the optic disc may be estimated based on the remaining portions of the summation vectors, other than portions in which the values of the horizontal axis and vertical axis summation vectors correspond to '0'.

Figure 14:
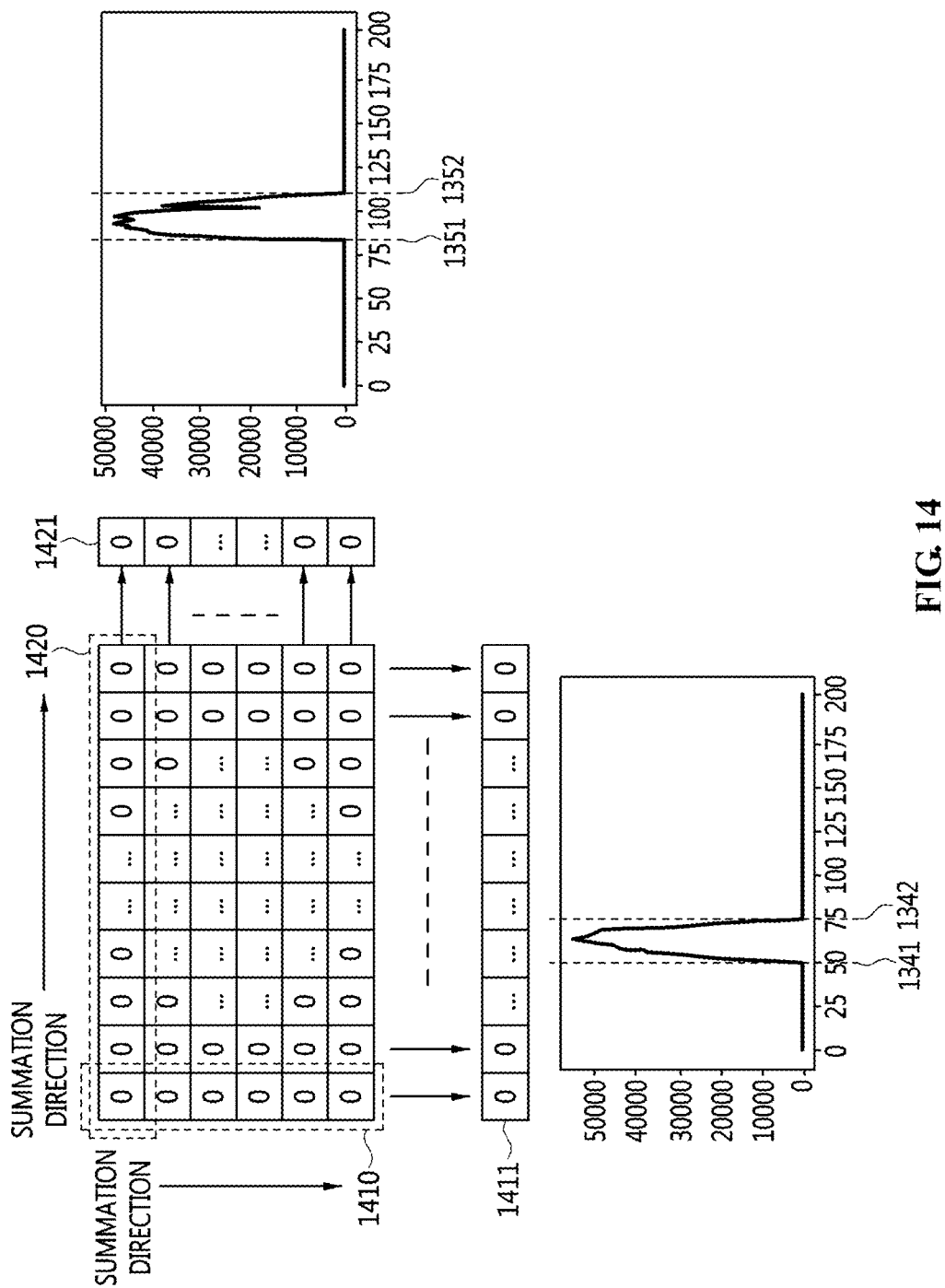

For example, referring to FIG. 14, it can be seen that the values of the binary image pixel value matrix 1320, except for the optic disc, appear as '0'. That is, a portion in which a summation column vector value 1411 or a summation row vector value 1421, obtained by summing values in a summation column 1410 or summing values in a summation row 1420, corresponds to '0' may mean that information about the optic disc is not contained in the preprocessed image 1311.

Therefore, as illustrated in FIG. 13, portions in which the value of the horizontal axis summation vector 1331 changes to be greater than 0 in the horizontal axis summation vector floating graph 1315 may be detected as the locations of an optic disc-left tangent line 1341 and an optic disc-right tangent line 1342, respectively. Further, portions in which the value of the vertical axis summation vector 1332 changes to be greater than 0 in the vertical axis summation vector floating graph 1314 may be detected as the locations of an optic disc-upper tangent line 1351 and an optic disc-lower tangent line 1352, respectively.

Also, a portion detected first on the left side of a floating line in the horizontal axis summation vector floating graph 1315 may be determined to be the location of the optic disc-left tangent line 1341, and a portion detected first on the right side of the floating line may be determined to be the location of the optic disc-right tangent line 1342. Further, a portion detected first on the upper side of a floating line in the vertical axis summation vector floating graph 1314 may be determined to be the location of the optic disc-upper tangent line 1351, and a portion detected first on the lower side of the floating line may be determined to be the location of the optic disc-lower tangent line 1352.

In this case, the radius of the circle corresponding to the boundary of the optic disc may be estimated using a distance between the detected optic disc-left tangent line 1341 and the optic disc-right tangent line 1342 or a distance between the optic disc-upper tangent line 1351 and the optic disc-lower tangent line 1352.

Thereafter, multiple capture areas for generating multiple transformed images may be designated within a range preset based on the optic disc detected from the preprocessed image.

First, each of the multiple capture areas may have the shape of a square having sides of a preset length in consideration of the size of the optic disc and have the center of gravity thereof located on the circumference of a virtual circle having the center of the optic disc as the center of the virtual circle, wherein the radius of the virtual circle may be greater than that of a circle corresponding to the boundary of the optic disc.

Hereinafter, a procedure for designating multiple capture areas will be described in detail with reference to FIG. 12.

Referring to FIG. 12, a virtual circle 1220 having a radius greater than that of a circle corresponding to an optic disc boundary 1210 may be generated. Here, N points may be randomly extracted from the circumference of the virtual circle 1220, and may be set as the centers 1220-1 to 1220-8 of gravity for capture areas.

Here, any one point on the circumference of the virtual circle may be set as a reference point, and multiple centers of gravity corresponding to multiple capture areas may be set while moving at a preset angle from the reference point. For example, assuming that the preset angle is 30°, a total of 12 centers of gravity may be set.

Here, squares having the set centers 1220-1 to 1220-8 of gravity for the capture areas as centers and having sides of a preset length may correspond to capture areas 1231 to 1233. Although only three capture areas 1231 to 1233 are depicted in FIG. 12, eight capture areas may be set to correspond to eight centers of gravity because a total of eight centers 1220-1 to 1220-8 of gravity for the capture areas are present in FIG. 12.

At this time, the length of one side of each of the capture areas 1231 to 1233 may be set to a value greater than the radius of the circle corresponding to the optic disc boundary 1210 so that the optic disc can be included in the capture areas 1231 to 1233.

Here, multiple captured images may be generated by capturing images of the multiple capture areas, and multiple transformed images may be generated by performing rotation and channel separation on each of the multiple captured images.

Figure 15:
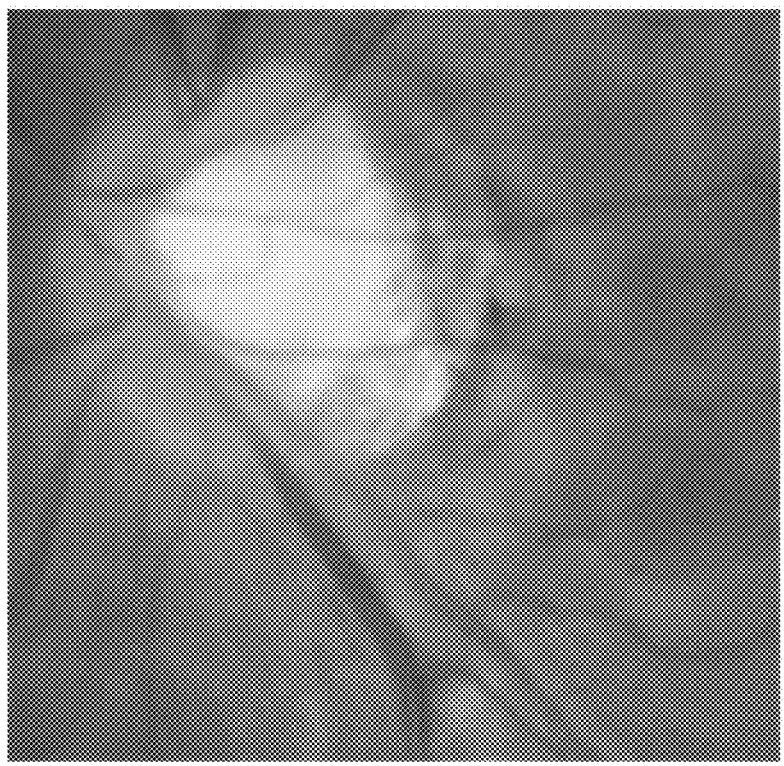
FIG. 15 is a diagram illustrating an example of a captured area according to the present invention.

For example, when images of the multiple capture areas are captured, the captured image, such as that shown in FIG. 15, may be generated.

Figure 16:
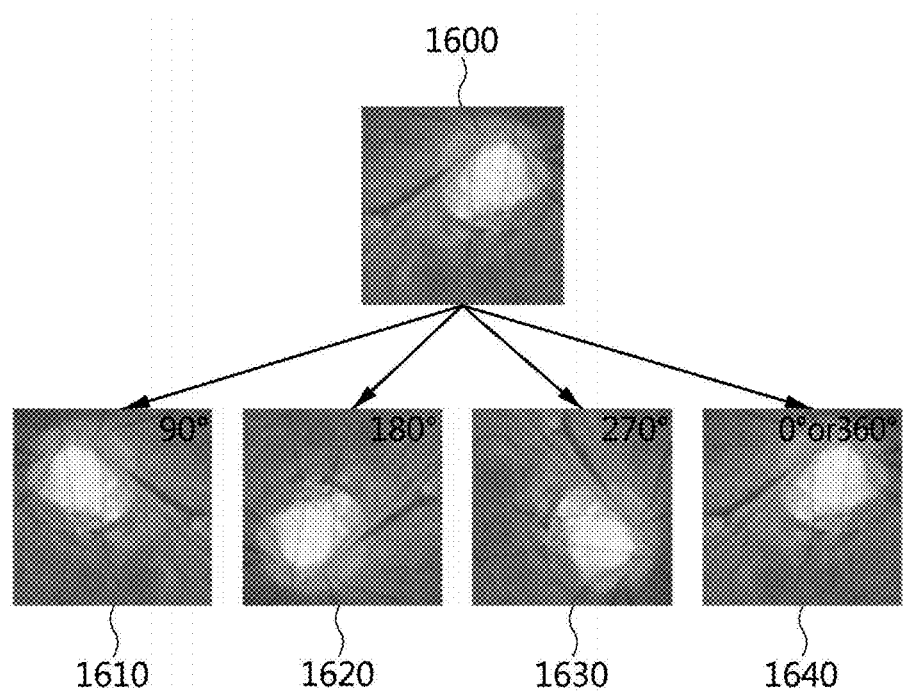
FIGS. 16 and 17 are diagrams illustrating an example of a data amplification procedure according to the present invention.
Figure 17:
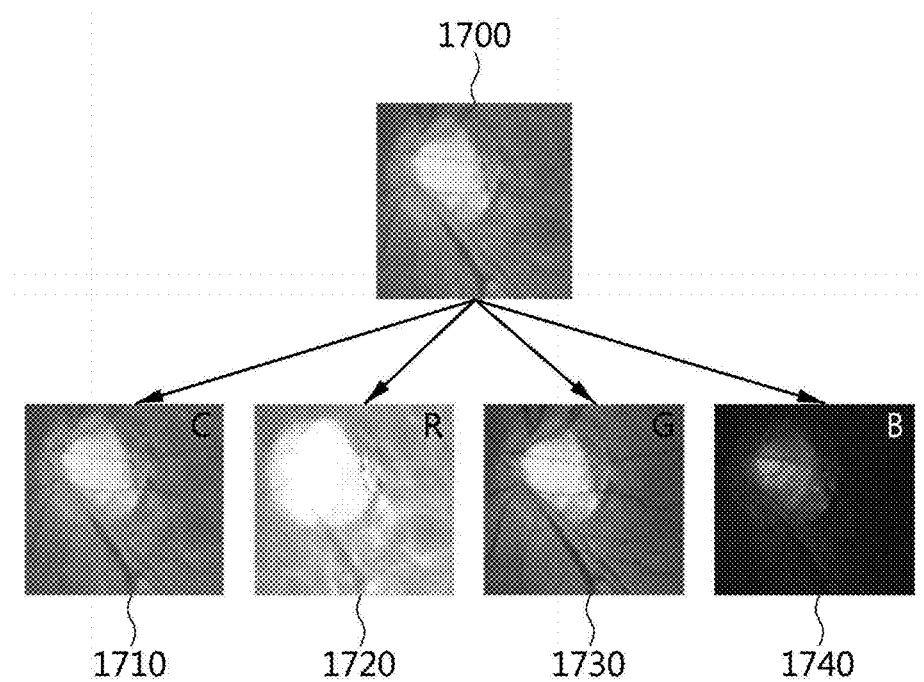

In this case, multiple transformed images 1610 to 1640 and 1710 to 1740 may be generated by performing rotation and channel separation on each of the multiple captured images, as illustrated in FIGS. 16 and 17.

Referring to FIG. 16, transformed images, generated via rotation, may include a transformed image 1610 obtained by rotating a captured image 1600 at an angle of 90°, a transformed image 1620 obtained by rotating the captured image 1600 at an angle of 180°, and a transformed image 1630 obtained by rotating the captured image 1600 at an angle of 270°, and may also include a transformed image 1640 that is obtained by rotating the captured image 1600 at an angle of 360° and that has the same shape as the captured image 1600.

Referring to FIG. 17, transformed images, generated via channel separation, may include a transformed image 1720 obtained by separating only an R channel from a captured image 1700, a transformed image 1730 obtained by separating only a G channel from the captured image 1700, and a transformed image 1740 obtained by separating only a B channel from the captured image 1700, and may also include a transformed image 1710 obtained without channel separation.

In this case, the present invention may also generate multiple transformed images by performing rotation and channel separation on the preprocessed image.

Figure 18:
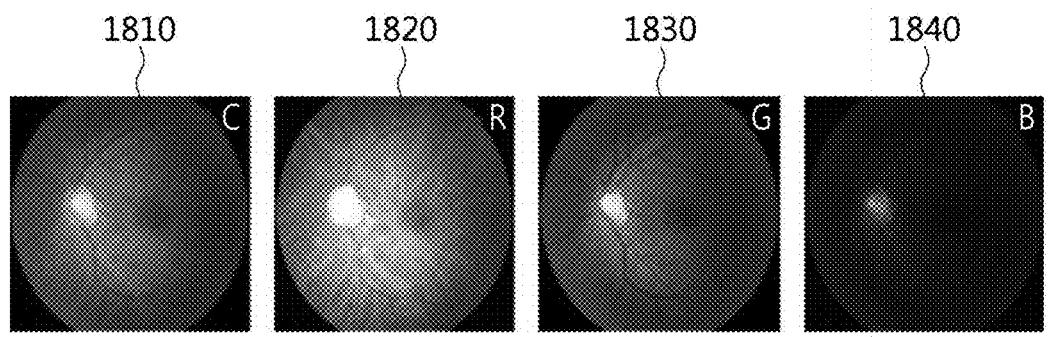
FIGS. 18 to 23 are diagrams illustrating examples of multiple transformed images according to the present invention.

For example, as illustrated in FIG. 18, transformed images corresponding to a color image 1810, an R-channel image 1820, a G-channel image 1830, and a B-channel image 1840 may be generated by performing channel separation on the preprocessed image.

Figure 19:
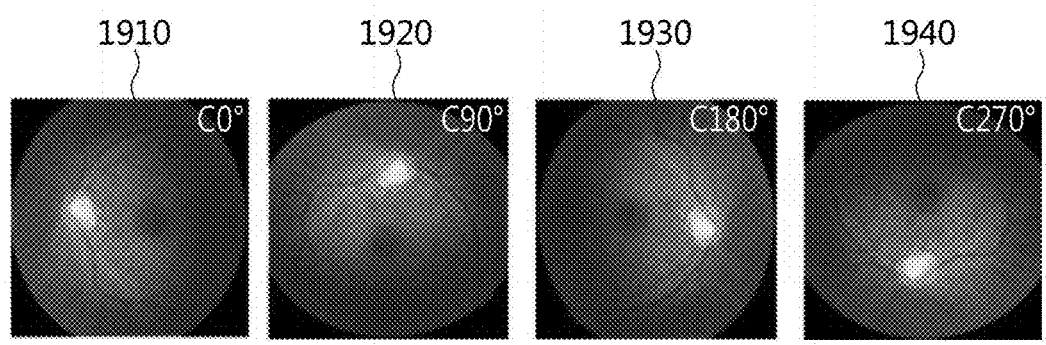
Figure 20:
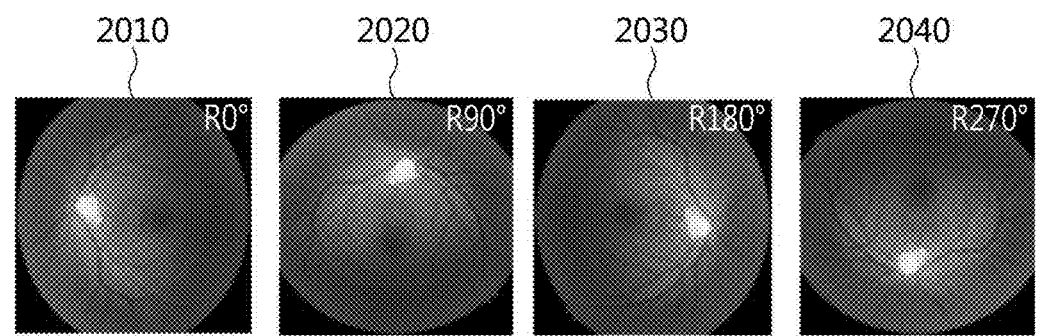

In another example, transformed images 1910 to 1940, such as those illustrated in FIG. 19, may be generated by rotating the color image 1810, which is generated by performing channel separation on the preprocessed image. Alternatively, transformed images 2010 to 2040, such as those illustrated in FIG. 20, may be generated by rotating the R channel image 1820, which is generated by performing channel separation on the preprocessed image.

Figure 21:
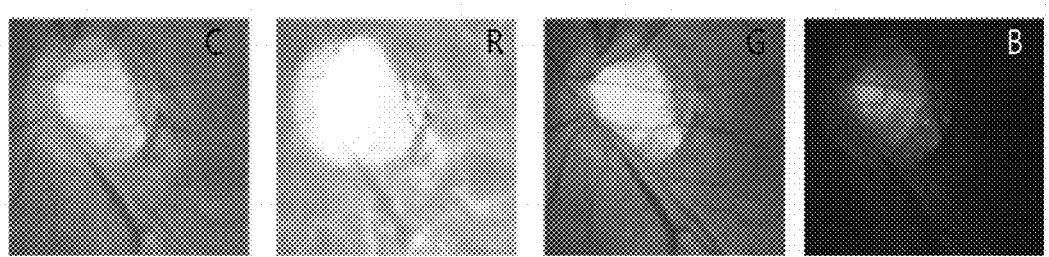
Figure 22:
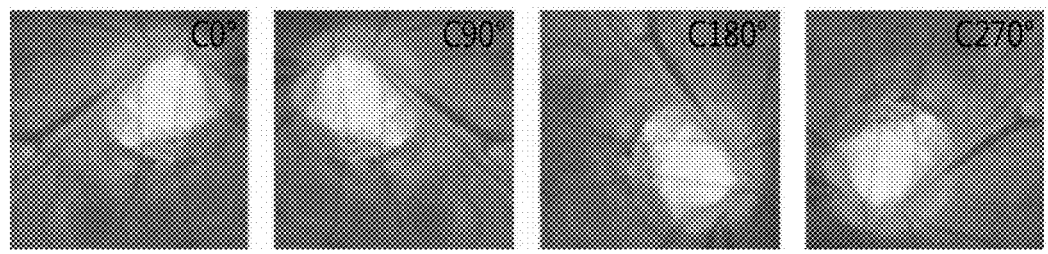
Figure 23:
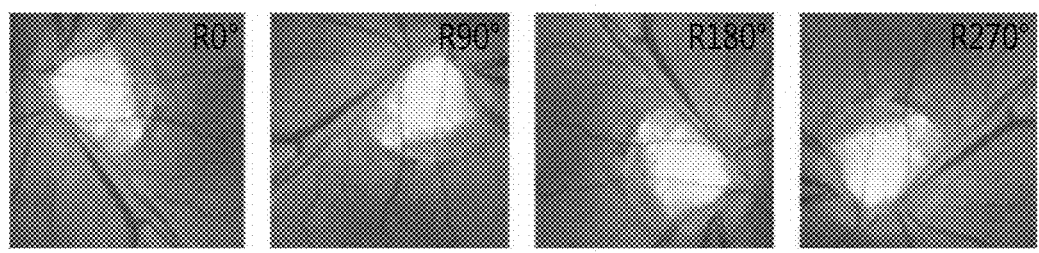

Here, as illustrated in FIGS. 21 to 23, various types of transformed images may be generated by performing, in combination, rotation and channel separation on the captured image as well.

In this way, data amplification is performed, multiple transformed images may be generated from one original fundus image, and the present invention may use the acquired transformed images as learning data for machine learning.

That is, the glaucoma diagnosis method according to the embodiment of the present invention allows multiple individual learning models of different types to be learned based on the multiple transformed images, and generates a glaucoma determination model based on respective outputs of the learned multiple individual learning models at step S520.

Figure 24:
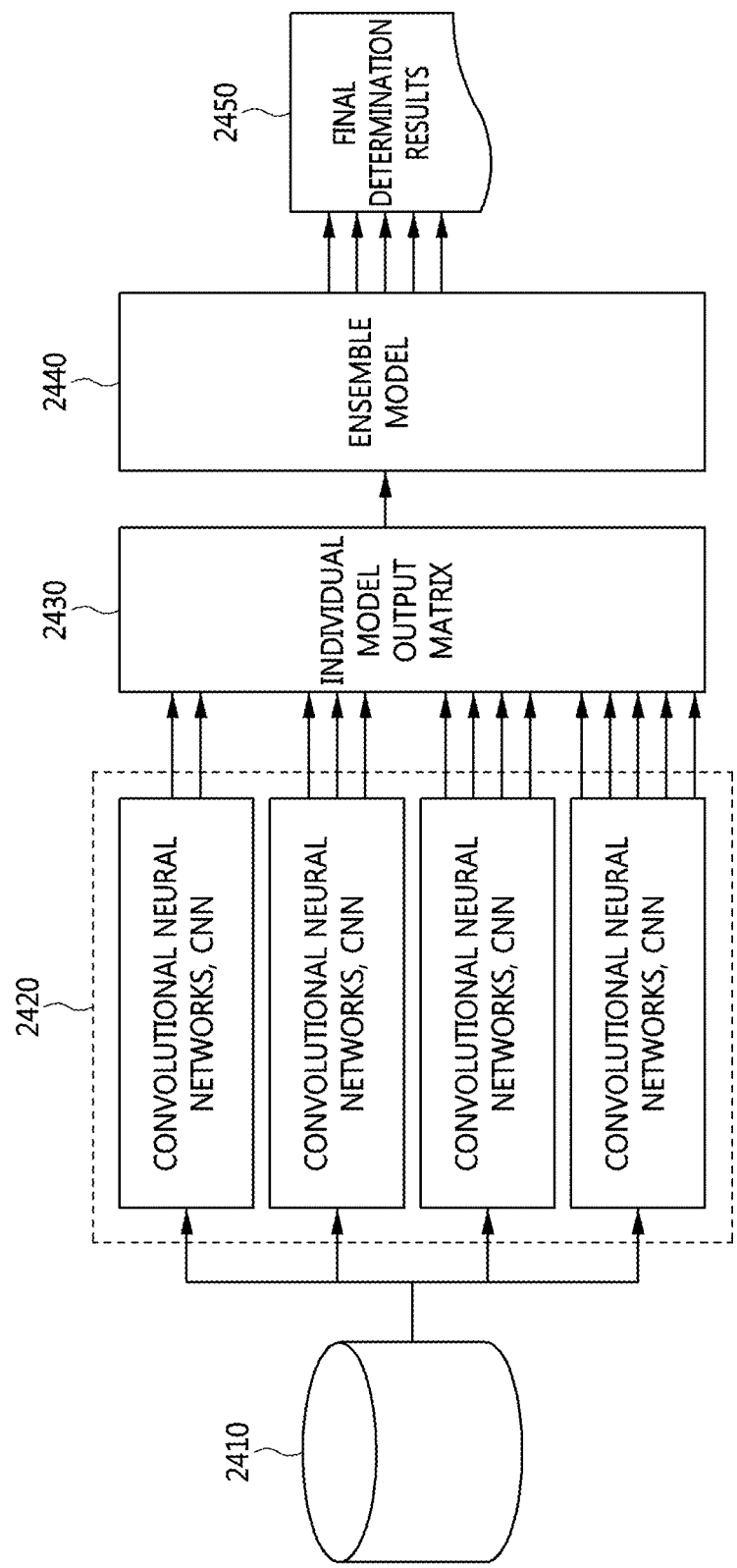
FIGS. 24 and 25 are diagrams illustrating an example of a glaucoma class diagnosis process using multiple individual learning models and a glaucoma determination model according to the present invention.

For example, through the learning procedure having the structure illustrated in FIG. 24, an ensemble model 2440 corresponding to the glaucoma determination model may be generated.

Referring still to FIG. 24, multiple individual learning models 2420 may correspond to Convolutional Neural Networks (CNN), and may be different from each other in at least one of the number of hidden layers in the corresponding CNN, the type of input data, and the number of outputs.

Here, setting input data differently may be the operation of configuring different subsets based on multiple transformed images, depending on the detailed method applied to the data amplification procedure, and arranging respective subsets in the individual learning models. For example, assuming that four individual learning models 2420 are present, as illustrated in FIG. 24, four different subsets may be configured based on multiple transformed images 2410. Thereafter, input data to be input for individual learning models may be differently set by arranging different subsets in the individual learning models 2420.

Here, the output grades of the individual learning models 2420 may be variously configured. For example, the output grades of the multiple individual learning models according to the present invention may be equal to or greater than a third grade having at least three outputs.

In an embodiment, an individual learning model having an output grade corresponding to a fifth grade may have five outputs, corresponding to Normal N, preperimetric glaucoma G0, Stage1 Glaucoma G1, Stage2 Glaucoma G2, and Stage3 Glaucoma G3, and may perform machine learning based on the five outputs.

In another embodiment, an individual learning model having an output grade corresponding to a third grade may have three outputs corresponding to {N}, {G0, G1}, and {G2, G3}.

In a further embodiment, although it may not be applied to the present invention, an individual learning model having an output grade corresponding to a second grade may have two outputs corresponding to {N} and {G0, G1, G2, G3}, {N} and {G0, G1}, or {N, G0} and {G1, G2, G3}.

At this time, the glaucoma determination model may be generated based on a matrix into which respective outputs of the learned multiple individual learning models are digitized and integrated.

For example, as illustrated in FIG. 24, an ensemble model 2440 corresponding to a glaucoma determination model may be generated based on an individual model output matrix 2430. That is, when the ensemble model 2440, which uses the individual model output matrix 2430 as machine-learning data, is optimized, the generation of a final glaucoma determination model may be completed. Here, as the methods for configuring the ensemble model 2440, a Support Vector Machine (SVM), an Artificial Neural Network (ANN), eXtreme Gradient Boosting (XGB), Convolutional Neural Network (CNN) or the like may be used.

Next, the glaucoma diagnosis method according to the embodiment of the present invention diagnoses the class of glaucoma for the original fundus image based on the glaucoma determination model at step S530.

Figure 25:
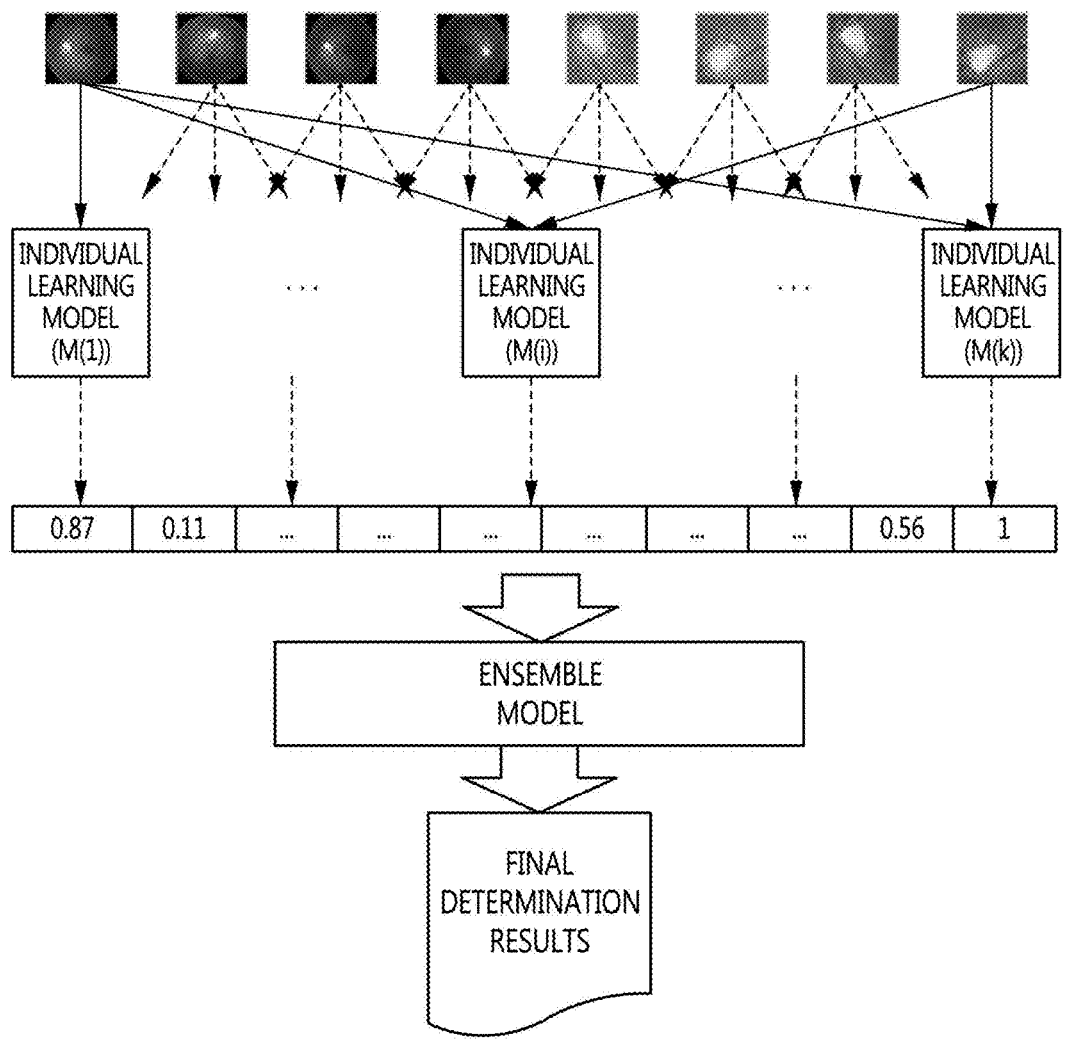

That is, referring to FIG. 25, multiple transformed images generated from the original fundus image are input to multiple individual learning models in accordance with different input values, and final determination results corresponding to the classes of glaucoma may be output based on the ensemble model, which corresponds to a matrix obtained by digitizing and integrating the outputs of the multiple individual learning models.

For example, glaucoma classes may be diagnosed to be classified into a normal class, preperimetric glaucoma, primary glaucoma, secondary glaucoma, tertiary glaucoma, etc., and may be output to a doctor or a patient via a monitor or a screen.

Furthermore, the results of the finally determined glaucoma class diagnosis may be recorded and stored in a storage module.

Although not illustrated in FIG. 5, the glaucoma diagnosis method according to the embodiment of the present invention may store various types of information generated during a glaucoma diagnosis process according to the embodiment of the present invention in a separate storage module.

By means of the glaucoma diagnosis method, a screening test for preperimetric glaucoma and early glaucoma may be performed.

Furthermore, micro-defects in RNFL may be automatically identified, and thus the severity of glaucoma may be classified and diagnosed.

Furthermore, the quality of medical service may be improved and the expenditure of related medical costs may be reduced while the risk of blindness may be decreased, and thus social costs attributable to blindness may also be decreased.

Figure 26:
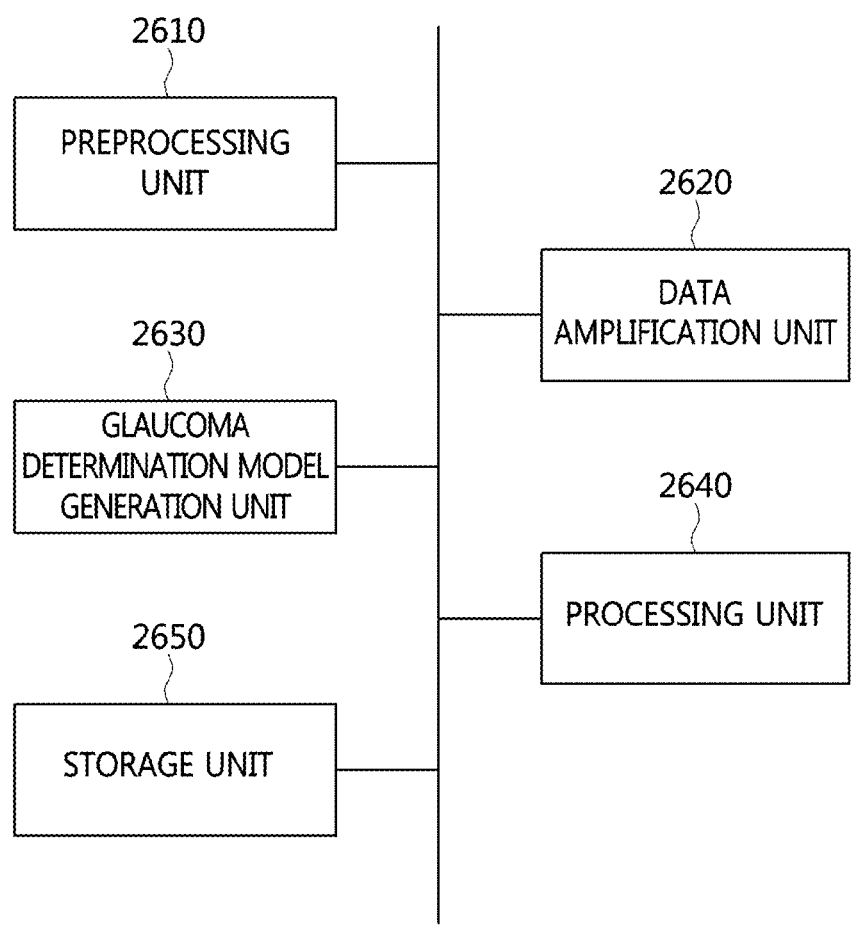
FIG. 26 is a block diagram illustrating a glaucoma diagnosis apparatus according to an embodiment of the present invention.

FIG. 26 is a block diagram illustrating a glaucoma diagnosis apparatus according to an embodiment of the present invention.

Referring to FIG. 26, the glaucoma diagnosis apparatus according to the embodiment of the present invention includes a preprocessing unit 2610, a data amplification unit 2620, a glaucoma determination model generation unit 2630, a processing unit 2640, and a storage unit 2650.

The preprocessing unit 2610 generates a preprocessed image for an original fundus image.

Here, the original fundus image may be an image obtained by capturing an image of the retina of a patient using a fundus scope or a fundus camera, and may be captured as illustrated in FIG. 6.

The original fundus image, such as that illustrated in FIG. 6, may be a three-channel color image, and may be data that is basically input in order to determine whether glaucoma is present or to classify the severity of glaucoma.

Here, the preprocessed image may be generated through a procedure of performing preprocessing on the original fundus image. Such a preprocessing procedure may be configured to eliminate unnecessary information present in the original fundus image and to convert the original fundus image into information in a state usable for machine learning for diagnosing glaucoma.

Here, the preprocessed image may be generated by individually detecting a left tangent line and a right tangent line of a fundus based on 2D matrix values generated based on binarized pixel values of the original fundus image and by deleting unnecessary areas that do not contain fundus information with respect to the left tangent line and the right tangent line.

For example, the preprocessing procedure may be a procedure for recognizing information about a fundus-left tangent line 711, a fundus-right tangent line 712, an information non-inclusion area 720, a fundus area 730, an optic disc 740, and a fundus center 750, which are included in the original fundus image, as illustrated in FIG. 7, and for deleting areas unnecessary for the determination of glaucoma based on the recognized information.

Here, the unnecessary areas may mean areas located outside the fundus-left tangent line 711 and the fundus-right tangent line 712 illustrated in FIG. 7, that is, areas that do not contain fundus information. Therefore, as illustrated in FIG. 8, the preprocessed image may be generated by deleting unnecessary areas 811 and 812 that do not contain fundus information.

Although the information non-inclusion area 720 illustrated in FIG. 7 does not contain fundus information, similar to the unnecessary areas 811 and 812 illustrated in FIG. 8, it is located inside the fundus-left tangent line 711 and the fundus-right tangent line 712, and thus the information non-inclusion area 720 is not deleted in the preprocessing procedure. Therefore, the information non-inclusion area 720 may be utilized for indicating separate marking information such as the image number or capture date of the corresponding fundus image.

The core of the preprocessing procedure is to detect the fundus-left tangent line and the fundus-right tangent line from the original fundus image and to extract an area therebetween.

Therefore, with reference to FIGS. 9 to 11, a procedure for detecting the fundus-left tangent line and the fundus-right tangent line from the original fundus image will be described in detail below.

First, referring to FIG. 9, an original fundus image (Picture Original: PO) 911 may be converted into the format of a grey fundus image (Picture Grey: PG) 912. Here, data of the grey fundus image 912 may have a 2D matrix structure. Therefore, the matrix may be binarized back based on a specific threshold value (ThresHoldBinary: THB), and may be converted into a binary fundus image (Picture Binary: PB) 913. Since the binary fundus image 913 may also have a 2D matrix data structure, the pixels of the binary fundus image 913 may be represented by a matrix, that is, a binary image pixel value matrix 920. In this case, as illustrated in FIG. 10, values in the binary image pixel value matrix are summed in the direction of a horizontal axis, and a horizontal axis summation vector 930 corresponding to the results of summation in the horizontal axis may float on a 2D plane, and thus a horizontal axis summation vector floating graph 914 may be acquired. Here, referring to the summation vector 930 or the horizontal axis summation vector floating graph 914, it can be seen that all values except for values in the fundus area 730, such as that shown in FIG. 7, appear as '0'. That is, a portion in which a summation column vector value 1011, obtained by summing values in a summation column 1010, as shown in FIG. 10, is '0' means that fundus information is not included in the portion corresponding to the summation column 1010 in the original fundus image 911, and may then be determined to be an unnecessary area.

Therefore, as illustrated in FIG. 11, portions in which the value of the horizontal axis summation vector changes to be greater than 0 in the horizontal axis summation vector floating graph 914 may be detected as the locations of a fundus-left tangent line 941 and a fundus-right tangent line 942. Here, a portion detected first on the left side of a floating line in the horizontal axis summation vector floating graph 914 is determined to be the location of the fundus-left tangent line 941, and a portion detected first on the right side of the floating line is determined to be the location of the fundus-right tangent line 942.

The data amplification unit 2620 may generate multiple transformed images for the original fundus image based on the preprocessed image.

In the present invention, a data amplification task for receiving the preprocessed image, acquired through the above-described preprocessing procedure, as input and generating multiple transformed images may be performed.

Here, the purpose of data amplification is to provide learning data required in order to allow model parameters, which are targets to be optimized, to be sufficiently learned during a process for constructing the glaucoma determination model. Also, the effect of eliminating dependence of the glaucoma determination model on specific data may be expected by providing various types of learning data based on data amplification.

The task to be performed first for data amplification is to detect an optic disc from the preprocessed image and estimate an external boundary line of the optic disc. That is, in the present invention, whether an RNFL defect is present must be determined in order to detect preperimetric glaucoma or early glaucoma. In this case, the RNFL may correspond to the optic nerve, and the optic disc may correspond to a portion in which the retina is connected to the optic nerve, and thus the approximate location of the RNFL may be determined by detecting the optic disc from the preprocessed image.

Here, the optic disc may correspond to the brightest portion, among portions of the fundus image included in the preprocessed image, as illustrated in FIG. 12. Below, a procedure for estimating the center and the boundary of the optic disc from the preprocessed image will be described in detail with reference to FIGS. 13 and 14.

First, the preprocessed image may be binarized into a binary image, and the center and boundary of the optic disc may be estimated based on respective summation vectors of the horizontal axis and the vertical axis of a matrix that indicates the pixel values of the binary image.

For example, referring to FIG. 13, a preprocessed image 1311 may be converted into a grey preprocessed image (picture grey) 1312. Here, the data of the grey preprocessed image 1312 may have a 2D matrix structure. Therefore, the matrix is binarized back based on a specific threshold value THO, and may then be converted into a binary preprocessed image 1313. Here, since the binary preprocessed image 1313 may also have a 2D matrix data structure, the pixels of the binary preprocessed image 1313 are represented by a matrix, that is, a binary image pixel value matrix 1320.

Here, as illustrated in FIG. 13, values in the binary image pixel value matrix 1320 may be respectively summed for a horizontal axis and a vertical axis, and a horizontal axis summation vector 1331 and a vertical axis summation vector 1332, which correspond to respective summed results, may float on a 2D plane, and thus a horizontal axis summation vector floating graph 1315 and a vertical axis summation vector floating graph 1314 may be acquired.

Thereafter, the coordinates of the center of the optic disc may be estimated in accordance with the maximum value of the horizontal axis summation vector and the maximum value of the vertical axis summation vector. The radius of a circle corresponding to the boundary of the optic disc may be estimated based on the remaining portions of the summation vectors, other than portions in which the values of the horizontal axis and vertical axis summation vectors correspond to '0'.

For example, referring to FIG. 14, it can be seen that the values of the binary image pixel value matrix 1320, except for the optic disc, appear as '0'. That is, a portion in which a summation column vector value 1411 or a summation row vector value 1421, obtained by summing values in a summation column 1410 or summing values in a summation row 1420, corresponds to '0' may mean that information about the optic disc is not contained in the preprocessed image 1311.

Therefore, as illustrated in FIG. 13, portions in which the value of the horizontal axis summation vector 1331 changes to be greater than 0 in the horizontal axis summation vector floating graph 1315 may be detected as the locations of an optic disc-left tangent line 1341 and an optic disc-right tangent line 1342, respectively. Further, portions in which the value of the vertical axis summation vector 1332 changes to be greater than 0 in the vertical axis summation vector floating graph 1314 may be detected as the locations of an optic disc-upper tangent line 1351 and an optic disc-lower tangent line 1352, respectively.

Also, a portion detected first on the left side of a floating line in the horizontal axis summation vector floating graph 1315 may be determined to be the location of the optic disc-left tangent line 1341, and a portion detected first on the right side of the floating line may be determined to be the location of the optic disc-right tangent line 1342. Further, a portion detected first on the upper side of a floating line in the vertical axis summation vector floating graph 1314 may be determined to be the location of the optic disc-upper tangent line 1351, and a portion detected first on the lower side of the floating line may be determined to be the location of the optic disc-lower tangent line 1352.

In this case, the radius of the circle corresponding to the boundary of the optic disc may be estimated using a distance between the detected optic disc-left tangent line 1341 and the optic disc-right tangent line 1342 or a distance between the optic disc-upper tangent line 1351 and the optic disc-lower tangent line 1352.

Thereafter, multiple capture areas for generating multiple transformed images may be designated within a range preset based on the optic disc detected from the preprocessed image.

First, each of the multiple capture areas may have the shape of a square having sides of a preset length in consideration of the size of the optic disc and have the center of gravity thereof located on the circumference of a virtual circle having the center of the optic disc as the center of the virtual circle, wherein the radius of the virtual circle may be greater than that of a circle corresponding to the boundary of the optic disc.

Hereinafter, a procedure for designating multiple capture areas will be described in detail with reference to FIG. 12.

Referring to FIG. 12, a virtual circle 1220 having a radius greater than that of a circle corresponding to an optic disc boundary 1210 may be generated. Here, N points may be randomly extracted from the circumference of the virtual circle 1220, and may be set as the centers 1220-1 to 1220-8 of gravity for capture areas.

Here, any one point on the circumference of the virtual circle may be set as a reference point, and multiple centers of gravity corresponding to multiple capture areas may be set while moving at a preset angle from the reference point. For example, assuming that the preset angle is 30°, a total of 12 centers of gravity may be set.

Here, squares having the set centers 1220-1 to 1220-8 of gravity for the capture areas as centers and having sides of a preset length may correspond to capture areas 1231 to 1233. Although only three capture areas 1231 to 1233 are depicted in FIG. 12, eight capture areas may be set to correspond to eight centers of gravity because a total of eight centers 1220-1 to 1220-8 of gravity for the capture areas are present in FIG. 12.

At this time, the length of one side of each of the capture areas 1231 to 1233 may be set to a value greater than the radius of the circle corresponding to the optic disc boundary 1210 so that the optic disc can be included in the capture areas 1231 to 1233.

Here, multiple captured images may be generated by capturing images of the multiple capture areas, and multiple transformed images may be generated by performing rotation and channel separation on each of the multiple captured images.

For example, when images of the multiple capture areas are captured, the captured image, such as that shown in FIG. 15, may be generated.

In this case, multiple transformed images 1610 to 1640 and 1710 to 1740 may be generated by performing rotation and channel separation on each of the multiple captured images, as illustrated in FIGS. 16 and 17.

Referring to FIG. 16, transformed images, generated via rotation, may include a transformed image 1610 obtained by rotating a captured image 1600 at an angle of 90°, a transformed image 1620 obtained by rotating the captured image 1600 at an angle of 180°, and a transformed image 1630 obtained by rotating the captured image 1600 at an angle of 270°, and may also include a transformed image 1640 that is obtained by rotating the captured image 1600 at an angle of 360° and that has the same shape as the captured image 1600.

Referring to FIG. 17, transformed images, generated via channel separation, may include a transformed image 1720 obtained by separating only an R channel from a captured image 1700, a transformed image 1730 obtained by separating only a G channel from the captured image 1700, and a transformed image 1740 obtained by separating only a B channel from the captured image 1700, and may also include a transformed image 1710 obtained without channel separation.

In this case, the present invention may also generate multiple transformed images by performing rotation and channel separation on the preprocessed image.

For example, as illustrated in FIG. 18, transformed images corresponding to a color image 1810, an R-channel image 1820, a G-channel image 1830, and a B-channel image 1840 may be generated by performing channel separation on the preprocessed image.

In another example, transformed images 1910 to 1940, such as those illustrated in FIG. 19, may be generated by rotating the color image 1810, which is generated by performing channel separation on the preprocessed image. Alternatively, transformed images 2010 to 2040, such as those illustrated in FIG. 20, may be generated by rotating the R channel image 1820, which is generated by performing channel separation on the preprocessed image.

Here, as illustrated in FIGS. 21 to 23, various types of transformed images may be generated by performing, in combination, rotation and channel separation on the captured image as well.

In this way, data amplification is performed, multiple transformed images may be generated from one original fundus image, and the present invention may use the acquired transformed images as learning data for machine learning.

The glaucoma determination model generation unit 2630 allows multiple individual learning models of different types to be learned based on the multiple transformed images, and generates a glaucoma determination model based on respective outputs of the learned multiple individual learning models.

For example, through the learning procedure having the structure illustrated in FIG. 24, an ensemble model 2440 corresponding to the glaucoma determination model may be generated.

Referring still to FIG. 24, multiple individual learning models 2420 may correspond to Convolutional Neural Networks (CNN), and may be different from each other in at least one of the number of hidden layers in the corresponding CNN, the type of input data, and the number of outputs.

Here, setting input data differently may be the operation of configuring different subsets based on multiple transformed images, depending on the detailed method applied to the data amplification procedure, and arranging respective subsets in the individual learning models. For example, assuming that four individual learning models 2420 are present, as illustrated in FIG. 24, four different subsets may be configured based on multiple transformed images 2410. Thereafter, input data to be input for individual learning models may be differently set by arranging different subsets in the individual learning models 2420.

Here, the output grades of the individual learning models 2420 may be variously configured. For example, the output grades of the multiple individual learning models according to the present invention may be equal to or greater than a third grade having at least three outputs.

In an embodiment, an individual learning model having an output grade corresponding to a fifth grade may have five outputs, corresponding to Normal N, preperimetric glaucoma G0, Stage1 Glaucoma G1, Stage2 Glaucoma G2, and Stage3 Glaucoma G3, and may perform machine learning based on the five outputs.

In another embodiment, an individual learning model having an output grade corresponding to a third grade may have three outputs corresponding to {N}, {G0, G1}, and {G2, G3}.

In a further embodiment, although it may not be applied to the present invention, an individual learning model having an output grade corresponding to a second grade may have two outputs corresponding to {N} and {G0, G1, G2, G3}, {N} and {G0, G1}, or {N, G0} and {G1, G2, G3}.

At this time, the glaucoma determination model may be generated based on a matrix into which respective outputs of the learned multiple individual learning models are digitized and integrated.

For example, as illustrated in FIG. 24, an ensemble model 2440 corresponding to a glaucoma determination model may be generated based on an individual model output matrix 2430. That is, when the ensemble model 2440, which uses the individual model output matrix 2430 as machine-learning data, is optimized, the generation of a final glaucoma determination model may be completed. Here, as the methods for configuring the ensemble model 2440, a Support Vector Machine (SVM), an Artificial Neural Network (ANN), eXtreme Gradient Boosting (XGB), Convolutional Neural Network (CNN) or the like may be used.

The processing unit 2640 diagnoses the class of glaucoma for the original fundus image based on the glaucoma determination model.

That is, referring to FIG. 25, multiple transformed images generated from the original fundus image are input to multiple individual learning models in accordance with different input values, and final determination results corresponding to the classes of glaucoma may be output based on the ensemble model, which corresponds to a matrix obtained by digitizing and integrating the outputs of the multiple individual learning models.

For example, glaucoma classes may be diagnosed to be classified into a normal class, preperimetric glaucoma, primary glaucoma, secondary glaucoma, tertiary glaucoma, etc., and may be output to a doctor or a patient via a monitor or a screen.

The storage unit 2650 stores the multiple individual learning models and the glaucoma determination model. Further, the storage unit 2650 may also store and retain the results of the finally determined glaucoma class diagnosis.

Also, the storage unit 2650 may support a function for glaucoma diagnosis according to an embodiment of the present invention, as described above. Here, the storage unit 2650 may function as separate large-capacity storage or may include a control function for performing operations.

Meanwhile, the glaucoma diagnosis apparatus may be equipped with memory, and may store information in the memory therein. In an embodiment, the memory may be a computer-readable storage medium. In an embodiment, the memory may be a volatile memory unit. In another embodiment, the memory may be a nonvolatile memory unit. In an embodiment, a storage device may be a computer-readable storage medium. In various different embodiments, the storage device may include, for example, a hard disk device, an optical disk device or any type of additional large-capacity storage device.

By means of the glaucoma diagnosis apparatus, a screening test for preperimetric glaucoma and early glaucoma may be performed.

Further, micro-defects in RNFL may be automatically identified, and thus the severity of glaucoma may be classified and diagnosed.

Furthermore, the quality of medical service may be improved and the expenditure of related medical costs may be reduced while the risk of blindness may be decreased, and thus social costs attributable to blindness may also be decreased.

Figure 27:
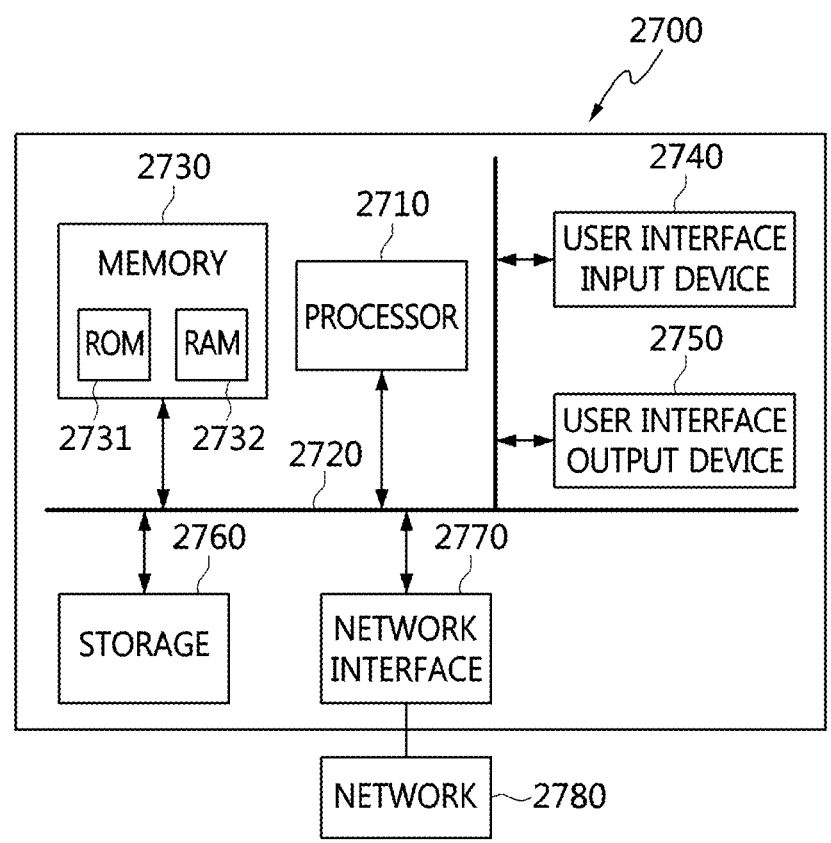
FIG. 27 is a diagram illustrating a computer system according to an embodiment of the present invention.

FIG. 27 is a diagram illustrating a computer system according to an embodiment of the present invention.

Referring to FIG. 27, the embodiment of the present invention may be implemented in a computer system such as a computer-readable storage medium. As illustrated in FIG. 27, a computer system 2700 may include one or more processors 2710, memory 2730, a user interface input device 2740, a user interface output device 2750, and storage 2760, which communicate with each other through a bus 2720. The computer system 2700 may further include a network interface 2770 connected to a network 2780. Each processor 2710 may be a Central Processing Unit (CPU) or a semiconductor device for executing processing instructions stored in the memory 2730 or the storage 2760. Each of the memory 2730 and the storage 2760 may be any of various types of volatile or nonvolatile storage media. For example, the memory 2730 may include Read-Only Memory (ROM) 2731 or Random Access Memory (RAM) 2732.

Therefore, the embodiment of the present invention may be implemented as a non-transitory computer-readable medium in which a computer-implemented method is recorded or in which computer-executable instructions are recorded. When the computer-executable instructions are executed by the processor, the instructions may perform the method according to at least one aspect of the present invention.

In accordance with the present invention, there can be provided a glaucoma diagnosis method, which enables a screening test for preperimetric glaucoma and early glaucoma based on a fundus image, which has excellent medical accessibility while decreasing diagnostic test costs.

Further, the present invention may classify and diagnose the severity of glaucoma by automatically identifying a micro-defect in a Retinal Nerve Fiber Layer (RNFL) based on a deep-learning model that is capable of automatically classifying the severity of glaucoma.

Furthermore, the present invention may improve the quality of medical service in the future by providing technology that is capable of classifying the severity of glaucoma, and may decrease social costs attributable to blindness by decreasing the risk of blindness while reducing the expenditure of related medical costs.

Furthermore, the present invention may provide a glaucoma diagnosis function in the form of artificial intelligence-based Clinical Decision Support System (CDSS) software, which can be installed in a fundus scope, which is currently and widely popularized, or can be operated in conjunction with the fundus scope, thus enabling the glaucoma diagnosis function to be utilized in various fields.

In addition, the present invention may provide glaucoma diagnosis technology that can be utilized for an automated service for a glaucoma screening test, improve the efficiency and accuracy of reading the results of fundus photography (ophthalmography) conducted on a large scale, and pass the time-saving benefit obtained from such improvement on to a specialist performing secondary determination, thus resulting in a more economical and accurate medical examination.

As described above, in the glaucoma diagnosis method using a fundus image and the apparatus for the same according to the present invention, the configurations and schemes in the above-described embodiments are not limitedly applied, and some or all of the above embodiments can be selectively combined and configured such that various modifications are possible.

What is claimed is:

1. A glaucoma diagnosis method, comprising:
    performing data amplification of generating multiple transformed images for an original fundus image based on a preprocessed image of the original fundus image;
    allowing multiple individual learning models of different types to be learned based on the multiple transformed images and generating a glaucoma determination model based on respective outputs of the learned multiple individual learning models; and
    diagnosing a class of glaucoma for the original fundus image based on the glaucoma determination model,
    wherein performing the data amplification comprises designating multiple capture areas for generating the multiple transformed images within a range preset based on an optic disc detected from the preprocessed image,
    wherein each of the multiple capture areas has a shape of a square, having sides of a preset length, in consideration of a size of the optic disc and has a center of gravity thereof located on a circumference of a virtual circle having a center of the optic disc as a center of the virtual circle, wherein a radius of the virtual circle is greater than that of a circle corresponding to a boundary of the optic disc.

2. The glaucoma diagnosis method of claim 1, wherein output grades of the multiple individual learning models are equal to or greater than a third grade having at least three outputs.

3. The glaucoma diagnosis method of claim 1, wherein generating the glaucoma determination model is configured to generate the glaucoma determination model based on a matrix into which respective outputs of the learned multiple individual learning models are digitized and integrated.

4. The glaucoma diagnosis method of claim 1, wherein designating the multiple capture areas is configured to set any one point on the circumference of the virtual circle as a reference point and to set multiple centers of gravity corresponding to the multiple capture areas while moving at a preset angle from the reference point.

5. The glaucoma diagnosis method of claim 1, wherein performing the data amplification is configured to generate multiple captured images by capturing images of the multiple capture areas and generate the multiple transformed images by performing rotation and channel separation on each of the multiple captured images.

6. The glaucoma diagnosis method of claim 1, wherein performing data amplification further comprises binarizing the preprocessed image into a binary image and estimating the center and the boundary of the optic disc based on respective summation vectors of a horizontal axis and a vertical axis of a matrix indicating pixel values of the binary image.

7. The glaucoma diagnosis method of claim 6, wherein estimating the center and the boundary of the optic disc is configured to estimate coordinates of the center in accordance with a maximum value of the summation vector of the horizontal axis and a maximum value of the summation vector of the vertical axis and to estimate a radius of the circle corresponding to the boundary based on a remaining portion, other than portions in which values in respective summation vectors of the horizontal axis and the vertical axis correspond to '0'.

8. The glaucoma diagnosis method of claim 1, wherein the multiple individual learning models correspond to Convolutional Neural Networks (CNN) and are different from each other in at least one of a number of hidden layers in a corresponding CNN, a type of input data, and a number of outputs.

9. The glaucoma diagnosis method of claim 1, further comprising performing preprocessing of generating the preprocessed image by respectively detecting a fundus-left tangent line and a fundus-right tangent line based on two-dimensional (2D) matrix values generated based on binarized pixel values of the original fundus image and by deleting an unnecessary area that does not include information about the fundus with respect to the left tangent line and the right tangent line.

10. A glaucoma diagnosis apparatus, comprising:
    a preprocessing unit for generating a preprocessed image of an original fundus image;
    a data amplification unit for generating multiple transformed images for the original fundus image based on the preprocessed image;
    a glaucoma determination model generation unit for allowing multiple individual learning models of different types to be learned based on the multiple transformed images and generating a glaucoma determination model based on respective outputs of the learned multiple individual learning models;

a processing unit for diagnosing a class of glaucoma for the original fundus image based on the glaucoma determination model; and a storage unit for storing the multiple individual learning models and the glaucoma determination model, wherein the data amplification unit designates multiple capture areas for generating the multiple transformed images within a range preset based on an optic disc detected from the preprocessed image, and wherein each of the multiple capture areas has a shape of a square, having sides of a preset length, in consideration of a size of the optic disc and has a center of gravity thereof located on a circumference of a virtual circle having a center of the optic disc as a center of the virtual circle, wherein a radius of the virtual circle is greater than that of a circle corresponding to a boundary of the optic disc.

11. The glaucoma diagnosis apparatus of claim 10, wherein output grades of the multiple individual learning models are equal to or greater than a third grade having at least three outputs.

12. The glaucoma diagnosis apparatus of claim 10, wherein the glaucoma determination model generation unit generates the glaucoma determination model based on a matrix into which respective outputs of the learned multiple individual learning models are digitized and integrated.

13. The glaucoma diagnosis apparatus of claim 10, wherein the data amplification unit sets any one point on the circumference of the virtual circle as a reference point, and sets multiple centers of gravity corresponding to the multiple capture areas while moving at a preset angle from the reference point.

14. The glaucoma diagnosis apparatus of claim 10, wherein the data amplification unit generates multiple captured images by capturing images of the multiple capture areas, and generates the multiple transformed images by performing rotation and channel separation on each of the multiple captured images.

15. The glaucoma diagnosis apparatus of claim 10, wherein the data amplification unit binarizes the preprocessed image into a binary image and estimates the center and the boundary of the optic disc based on respective summation vectors of a horizontal axis and a vertical axis of a matrix indicating pixel values of the binary image.

16. The glaucoma diagnosis apparatus of claim 15, wherein the data amplification unit estimates coordinates of the center in accordance with a maximum value of the summation vector of the horizontal axis and a maximum value of the summation vector of the vertical axis, and estimates a radius of the circle corresponding to the boundary based on a remaining portion, other than portions in which values in respective summation vectors of the horizontal axis and the vertical axis correspond to '0'.

* * * * *